(12) United States Patent  
Conte et al.

(10) Patent No.: US 7,928,106 B2
(45) Date of Patent: Apr. 19, 2011

(54) AZA-PYRIDOPYRIMIDINONE DERIVATIVES

(75) Inventors: Aurelia Conte, Basel (CH); Henrietta Dehmlow, Loerrach (DE); Uwe Grether, Efringen-Kirchen (DE); Nicole A. Kratochwil, Sool (CH); Holger Kuehne, Loerrach (DE); Robert Narquizian, Saint Louis (FR); Constantinos G. Panousis, Bottmingen (CH); Jens-Uwe Peters, Grenzach-Wyhlen (DE); Fabienne Ricklin, Hombourg (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 419 days.

(21) Appl. No.: 12/049,460

(22) Filed: Mar. 17, 2008

(65) Prior Publication Data
US 2008/0234277 A1    Sep. 25, 2008

(30) Foreign Application Priority Data

Mar. 23, 2007   (EP) .................................... 07104801

(51) Int. Cl.
*A61K 31/50* (2006.01)
*A61K 31/501* (2006.01)
*C07D 487/00* (2006.01)

(52) U.S. Cl. .................. 514/252.02; 544/236
(58) Field of Classification Search ........................ None
See application file for complete search history.

(56) References Cited

U.S. PATENT DOCUMENTS
5,167,949 A    12/1992   Ferrand et al.
2007/0275987 A1  11/2007   Conti et al.

FOREIGN PATENT DOCUMENTS
WO  WO 2005/077950    8/2005

OTHER PUBLICATIONS

Wolff et. al., "Burger's Medicinal Chemistry and Drug Discovery," 5th Ed. Part 1, pp. 975-977 (1995).*
Banker, et. al., Modern Pharmaceuticals, (1996) p. 596-7.*
Abarca et al., Tetrahedron, 45, pp. 7041-7048 (1989).
Zumbrunn et al., Synthetic Communications, 28, pp. 475-483 (1998).
Ferrand, G et al, *Euro. Jour. of Medicinal Chem.*, 31:4 (1996) 273-280 XP004040087.

* cited by examiner

*Primary Examiner* — James O Wilson
*Assistant Examiner* — Jeffrey H Murray
(74) *Attorney, Agent, or Firm* — George W. Johnston; Dennis P. Tramaloni; Brian C. Remy

(57) ABSTRACT

The invention is concerned with novel aza-pyridopyrimidinone derivatives of formula (I):

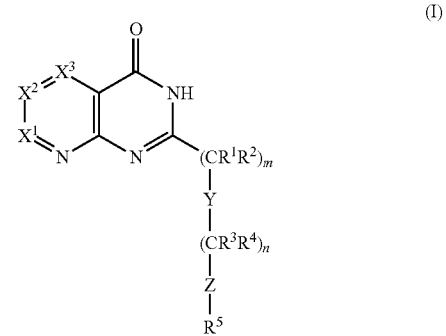

wherein $R^1$, $R^2$, $R^3$, $R^4$, $R^5$, $X^1$, $X^2$, $X^3$, Y, Z, m and n are as defined in the description and in the claims, as well as physiologically acceptable salts and esters thereof. These compounds are HM74A agonists and can be used in treating or preventing diseases which are modulated by HM74A agonists.

17 Claims, No Drawings

AZA-PYRIDOPYRIMIDINONE DERIVATIVES

PRIORITY TO RELATED APPLICATION(S)

This application claims the benefit of European Patent Application No. 07104801.1, filed Mar. 23, 2007, which is hereby incorporated by reference in its entirety.

BACKGROUND OF THE INVENTION

Coronary heart disease (CHD) remains the leading cause of death in Western countries. In the United States 13.2 million or 4.85% of the population is affected, with 1.2 million new or recurrent attacks and around 500 thousand deaths per year (American Heart Association, Statistics for 2001). The disease is influenced by several well-established risk factors, such as age, sex, blood lipids, blood pressure, smoking, diabetes, and body mass index (BMI) as an indicator of overweight and obesity. The National Cholesterol Education Program (NCEP) Adult Treatment Panel III defines elevated plasma levels of low density lipoprotein (LDL) cholesterol (LDL-C≧160 mg/dL), and low levels of high density lipoprotein (HDL) cholesterol (HDL-C≦40 mg/dL) as independent risk factors for CHD. Many prospective epidemiological studies have indicated that a decreased HDL-C level is a significant independent risk factor for heart disease, while increased HDL-C levels ≧60 mg/dL (≧1.55 mmol) have a protective role against CHD.

Nicotinic acid (Niacin), a vitamin of the B complex, is used for almost 40 years as a lipid-lowering drug with a favorable profile for all lipoprotein classes. Numerous clinical studies have shown the beneficial effects of niacin, demonstrating a reduction of coronary artery disease and overall mortality. Niacin is the most potent agent currently available to raise HDL. It has been proposed that niacin's main mode of action is through inhibition of lipolysis in the adipose tissue having as a result the reduction of free fatty acids (FFA) in plasma and liver and consequently the decreased production of very low density lipoproteins (VLDL), accounting for the reduction of total cholesterol (TC), triglycerides (TGs), and LDL-C. Due to the decreased TG rich lipoproteins levels, less modification of HDL particles occurs upon the action of cholesteryl ester transfer protein (CETP), resulting in a decreased catabolism of HDL. A direct inhibition of lipoprotein AI-HDL (LPAI-HDL) particle uptake by the liver has been also proposed, accounting for the overall HDL raising properties of niacin (Jin et al. Arterioscler. Thromb. Vasc. Biol. 1997, 17, 2020-2028).

Niacin also has anti-diabetic, anti-thrombotic and anti-inflammatory properties that contribute to the overall cardio-protective effects. Through a variety of mechanisms niacin reduces thrombosis, such as the reduction of lipoprotein (a) (Lp(a)) which is a potent inhibitor of fibrinolytic activity, and it is the only currently approved drug that effectively reduces the serum levels of Lp(a) (Carlson et al. J. Intern. Med. 1989, 17, 2020-8). Inflammation is a critical component of atherosclerosis, leading to recruitment of macrophages which both promote plaque development and decrease plaque stability thus increasing cardiovascular risk. Niacin has been suggested to have anti-inflammatory properties, such as the reduction of C-reactive protein (CRP) levels (Grundy et al. Arch. Intern. Med. 2002, 162, 1568-76). Several prospective studies have established a strong and direct correlation between cardiovascular risk and CRP levels, a measure of vascular inflammation. Extensive use of niacin has been hampered due to side effects, mainly intense cutaneous flushing.

HM74A/HM74, a G-protein coupled receptor (GPCR), was identified as a receptor for niacin and proposed as the mediator of the niacin effects (Wise et al. J. Biol. Chem. 2003, 278 (11) 9869-9874 and Soga et al Biochem Biophys Res Commun 2003 303 (1) 364-369). In support, deletion of the PUMA-G (HM74A orthologue) in mice abrogated the niacin effects on reduction of plasma free fatty acids and triglycerides (Tunaru et al. Nature Medicine 2003, (3) 352-255).

The novel compounds of the present invention exceed the compounds known in the art, inasmuch as they bind to and activate HM74A. The compounds of the present invention are selective for HM74A by which is meant that they show greater affinity for HM74A than for HM74. The compounds of the present invention are expected to have an enhanced therapeutic potential and exhibit reduced side effects compared to nicotinic acid.

SUMMARY OF THE INVENTION

The invention is concerned with the compounds of formula (I):

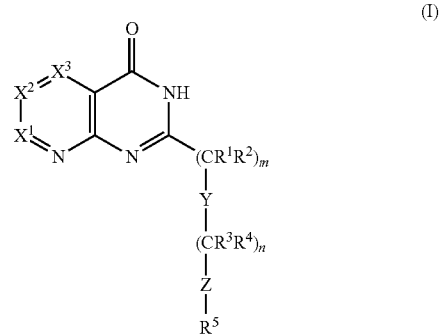

and pharmaceutically acceptable salts and esters thereof, wherein $X^1$, $X^2$, $X^3$, Y, Z, $R^1$-$R^5$, m and n are as defined in the detailed description and claims. In addition, the present invention relates to the methods of manufacturing and using the compounds of formula I as well as pharmaceutical compositions containing them. The compounds of formula I bind to and activate HM74A and therefore may be useful in treating or preventing diseases which are modulated by HM74A agonists. Examples of such diseases include increased lipid and cholesterol levels, particularly dyslipidemia, low HDL-cholesterol, atherosclerotic diseases, hypertriglyceridemia, thrombosis, angina pectoris, peripheral vascular disease, stroke, diabetes, particularly non-insulin dependent diabetes mellitus, metabolic syndrome, Alzheimer's disease, Parkinson's disease, schizophrenia, sepsis, inflammatory diseases (such as e.g. asthma, arthritis, colitis, pancreatitis, cholestasis/fibrosis of the liver, and diseases that have an inflammatory component such as e.g. Alzheimer's disease or impaired/improvable cognitive function).

DETAILED DESCRIPTION OF THE INVENTION

Unless otherwise indicated, the following definitions are set forth to illustrate and define the meaning and scope of the various terms used to describe the invention herein.

In this specification the term "lower" is used to mean a group having one to seven carbon atoms. In particular embodiments the lower group preferably has one to four carbon atom(s).

The term "halogen" refers to fluorine, chlorine, bromine or iodine. Preferably, the halogen is fluorine, chlorine or bromine.

The term "alkyl", alone or in combination with other groups, refers to a branched or straight-chain monovalent saturated aliphatic hydrocarbon radical of one to twenty carbon atoms. Preferably the alkyl has one to sixteen carbon atoms, more preferably one to ten carbon atoms. Lower-alkyl groups as described below are preferred alkyl groups.

The term "lower-alkyl", alone or in combination with other groups, refers to a branched or straight-chain monovalent alkyl radical of one to seven carbon atoms. Preferably the lower-alkyl has one to four carbon atoms. This term is further exemplified by such radicals as methyl, ethyl, n-propyl, iso-propyl, n-butyl, s-butyl, t-butyl and the like.

The term "fluoro-lower-alkyl" refers to lower-alkyl groups which are mono-substituted or multiply-substituted with fluorine. Examples of fluoro-lower-alkyl groups include $CFH_2$, $CF_2H$, $CF_3$, $CF_3CH_2$, $CF_3(CH_2)_2$, $(CF_3)_2CH$ and $CF_2H$—$CF_2$.

The term "alkenyl", alone or in combination with other groups, refers to a straight-chain or branched hydrocarbon residue comprising an olefinic bond and up to 20 carbon atoms. Preferably the alkenyl has up to 16 carbon atoms. The term "lower-alkenyl" refers to a straight-chain or branched hydrocarbon residue comprising an olefinic bond and up to 7 carbon atoms. Preferably the lower-alkenyl has up to 4 carbon atoms such as 2-propenyl.

The term "alkinyl", alone or in combination with other groups, stands for a straight-chain or branched hydrocarbon residue comprising a triple bond and up to 20 carbon atoms. Preferably the alkinyl has up to 16 carbon atoms. The term "lower-alkinyl" refers to a straight-chain or branched hydrocarbon residue comprising a triple bond and up to 7 carbon atoms. Preferably the alkinyl has up to 4 carbon atoms such as 2-propinyl.

The term "amino", alone or in combination, signifies a primary, secondary or tertiary amino group bonded via the nitrogen atom, with the secondary amino group carrying an alkyl or cycloalkyl substituent and the tertiary amino group carrying two similar or different alkyl or cycloalkyl substituents or the two substituents together forming a ring. Examples of an amino group include —$NH_2$, methylamino, ethylamino, dimethylamino, diethylamino, methyl-ethylamino, pyrrolidin-1-yl or piperidino etc. Preferred amino groups are primary amino groups, dimethylamino and diethylamino and particularly dimethylamino.

The term "cycloalkyl" refers to a monovalent carbocyclic radical of 3 to 10 carbon atoms. Preferably the cycloalkyl has 3 to 7 carbon atoms and more preferably 3 to 6 carbon atoms, such as cyclopropyl, cyclobutyl, cyclopentyl, or cyclohexyl.

The term "fluoro-cycloalkyl" refers to a cycloalkyl group as defined above, which is mono-substituted or multiply-substituted with fluorine. Preferably the cycloalkyl is substituted with 1 to 4 fluorine atoms. Examples of fluoro-cycloalkyl include 2-fluorocyclopropyl, 2,2-difluorocyclopropyl, 2,2,3,3-tetrafluorocyclopropyl, 3-fluorocyclobutyl, 3,3-difluorocyclobutyl, and 3,3-difluorocyclopentyl.

The term "alkoxy" refers to the group R'—O—, wherein R' is an alkyl. The term "lower-alkoxy" refers to the group R'—O—, wherein R' is a lower-alkyl.

The term "fluoro-lower-alkoxy" refers to the group R"—O—, wherein R" is fluoro-lower-alkyl. Examples of fluoro-lower-alkoxy groups include $CFH_2$—O, $CF_2H$—O, $CF_3$—O, $CF_3CH_2$—O, $CF_3(CH_2)_2$—O, $(CF_3)_2CH$—O, and $CF_2H$—$CF_2$—O.

The term "aryl", alone or in combination with other groups, relates to the phenyl or naphthyl group. Preferably the aryl is a phenyl group, which can, unless specifically stated otherwise, optionally be substituted by 1 to 5, preferably 1 to 3 substituents, independently selected from the group consisting of: halogen, lower-alkyl, fluoro-lower-alkyl, hydroxy-lower-alkyl, lower-alkoxy, fluoro-lower-alkoxy, cycloalkyl, carboxy, hydroxy, amino, $NO_2$, carboxy-lower-alkyl, lower-alkyl-carbonyl, lower-alkoxy-carbonyl, lower-alkoxy-carbonyl-lower-alkyl, $H_2NC(O)$, (H,lower-alkyl)NC(O), (lower-alkyl)$_2$NC(O), $H_2NC(O)$-lower-alkyl, (H, lower-alkyl)NC(O)-lower-alkyl, (lower-alkyl)$_2$NC(O)-lower-alkyl, $H_2N$-lower-alkyl, (H, lower-alkyl)N-lower-alkyl, (lower-alkyl)$_2$N-lower-alkyl, lower-alkyl-$SO_2$, lower-alkyl-$SO_2O$, lower-alkyl-$SO_2$—NH, lower-alkyl-$SO_2$—N(lower-alkyl), $H_2NSO_2$, (H,lower-alkyl)$NSO_2$, (lower-alkyl)$_2NSO_2$, cyano, cycloalkyl, lower-alkoxy-lower-alkyl, lower-alkenyl, lower-alkinyl, phenyl, phenyloxy and dioxo-lower-alkylene (forming a benzodioxyl group). Preferred substituents can be halogen, hydroxy, lower-alkyl, lower-alkoxy and fluoro-lower-alkyl. Furthermore, aryl groups can preferably be substituted as described in the description and claims below.

The term "heteroaryl" refers to an aromatic 5 to 6 membered monocyclic ring or 9 to 10 membered bicyclic ring which can comprise 1, 2 or 3 atoms independently selected from nitrogen, oxygen and sulphur. Examples of a heteroaryl include furyl, pyridinyl, pyridazinyl, pyrimidinyl, pyrazinyl, thienyl, isoxazolyl, oxazolyl, oxadiazolyl, imidazolyl, pyrrolyl, pyrazolyl, triazolyl, tetrazolyl, thiazolyl, isothiazolyl, 1,2,3-thiadiazolyl, benzoimidazolyl, indolyl, indazolyl, benzoisothiazolyl, benzoxazolyl, benzoisoxazolyl and quinolinyl. Preferred heteroaryl groups include pyridinyl, oxazolyl and triazolyl, particularly pyridinyl. A heteroaryl group may optionally have a substitution pattern as described earlier in connection with the term "aryl." Furthermore, heteroaryl groups can preferably be substituted as described in the description and claims below.

The term "pharmaceutically acceptable esters" embraces derivatives of the compounds of formula (I), in which a carboxy group has been converted to an ester. Lower-alkyl, hydroxy-lower-alkyl, lower-alkoxy-lower-alkyl, amino-lower-alkyl, mono- or di-lower-alkyl-amino-lower-alkyl, morpholino-lower-alkyl, pyrrolidino-lower-alkyl, piperidino-lower-alkyl, piperazino-lower-alkyl, lower-alkyl-piperazino-lower-alkyl and aralkyl esters are examples of suitable esters. The methyl, ethyl, propyl, butyl and benzyl esters are preferred esters. The methyl and ethyl esters are especially preferred. The term "pharmaceutically acceptable esters" furthermore embraces compounds of formula (I) in which hydroxy groups have been converted to the corresponding esters with inorganic or organic acids such as, nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

Compounds of formula (I) can form pharmaceutically acceptable acid addition salts. Examples of such pharmaceutically acceptable salts are salts of compounds of formula (I) with physiologically compatible mineral acids, such as hydrochloric acid, sulphuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid. The term "pharmaceutically acceptable salts" refers to such salts. Compounds of formula (I) can further form salts with bases. Examples of such salts are alkaline, earth-alkaline and ammonium salts such as, for example, Na—, K—, Ca— and trimethylammonium salt. The term "pharmaceutically acceptable salts" also refers to such salts. Salts obtained by the addition of an acid are preferred.

The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 0.1 mg to about 5,000 mg, 1 mg to about 1,000 mg, or 1 mg to 100 mg may be appropriate, although the upper limit may be exceeded when indicated. The daily dosage can be administered as a single dose or in divided doses, or for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention are contemplated. Supplementary active compounds can also be incorporated into the compositions.

Unless otherwise indicated, the term "a compound of the formula" or "a compound of formula" or "compounds of the formula" or "compounds of formula" means any compound selected from the genus of compounds as defined by the formula.

In detail, the present invention relates to compounds of formula (I):

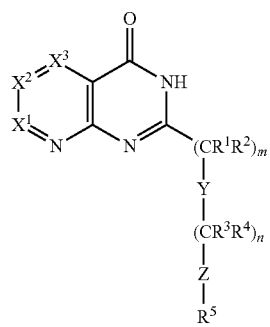

(I)

and pharmaceutically acceptable salts or esters thereof, wherein:
$X^1$ is N or $C(R^6)$; $X^2$ is N or $C(R^7)$; and $X^3$ is N or $C(R^8)$; wherein at least one of $X^1$, $X^2$ and $X^3$ is N; and wherein R6, R7, and R8 independently from each other are selected from the group consisting of:
(1) hydrogen,
(2) halogen,
(3) lower-alkyl,
(4) fluoro-lower-alkyl,
(5) lower-alkoxy,
(6) fluoro-lower-alkoxy, and
(7) cycloalkyl;
Y is selected from the group consisting of:
(1) a single bond,
(2) O,
(3) $N(R^9)C(O)$,
(4) $C(O)NR^9$,
(5) $N(R^9)C(O)O$,
(6) $OC(O)NR^9$,
(7) $N(R^9)C(O)NR^{10}$,
(8) $N(R^9)SO_2$, and
(9) $SO_2N(R^9)$;
wherein $R^9$ and $R^{10}$ independently from each other are selected from the group consisting of hydrogen, lower-alkyl and fluoro-lower-alkyl;
Z is a single bond, or, if n is 1, 2, 3, 4, 5 or 6, Z can also be O;
$R^1$, $R^2$, $R^3$ and $R^4$ independently from each other are selected from the group consisting of:
(1) hydrogen,
(2) fluoro,
(3) lower-alkyl, and
(4) fluoro-lower-alkyl; or
$R^1$ and $R^2$ are bound together with the carbon atom to which they are attached to form a ring of 3 to 7 carbon atoms; or $R^3$ and $R^4$ are bound together with the carbon atom to which they are attached to form a ring of 3 to 7 carbon atoms;
$R^5$ is aryl or heteroaryl, which aryl or heteroaryl is optionally substituted with 1 to 3 substituents independently selected from the group consisting of:
(1) halogen,
(2) lower-alkyl,
(3) lower-alkoxy,
(4) fluoro-lower-alkyl,
(5) fluoro-lower-alkoxy,
(6) cycloalkyl,
(7) fluoro-cycloalkyl,
(8) cycloalkyl-oxy,
(9) C(O)OH,
(10) lower-alkoxy-C(O),
(11) $NH_2C(O)$,
(12) N(H,lower-alkyl)C(O),
(13) N(lower-alkyl)$_2$C(O),
(14) OH,
(15) lower-alkyl-C(O)O,
(16) $NH_2$,
(17) N(H,lower-alkyl),
(18) N(lower-alkyl)$_2$,
(19) lower-alkyl-C(O)NH,
(20) lower-alkyl-C(O)N(lower-alkyl),
(21) $NH_2SO_2$,
(22) N(H,lower-alkyl)$SO_2$,
(23) N(lower-alkyl)$_2SO_2$,
(24) lower-alkyl-$SO_2$—NH,
(25) lower-alkyl-$SO_2$—N(lower-alkyl),
(26) cyano, and
(27) phenyl which is optionally substituted with 1 to 3 substituents independently selected from the group consisting of halogen, lower-alkyl, lower-alkoxy and fluoro-lower-alkyl;
m is 0, 1, 2 or 3; and n is 0, 1, 2, 3, 4, 5 or 6; wherein m+n is $\geq 1$, with the proviso that if $X^1$ is CH, $X^2$ is CH and $X^3$ is N, m+n is not 1.

Compounds of formula (I) are individually preferred and physiologically acceptable salts thereof are individually preferred and pharmaceutically acceptable esters thereof are individually preferred, with the compounds of formula (I) being particularly preferred.

The compounds of formula (I) can have one or more asymmetric C atoms and can therefore exist as an enantiomeric mixture, diastereomeric mixture or as optically pure compounds.

Preferred compounds of formula (I) according to the present invention are those, wherein only one of $X^1$, $X^2$ and $X^3$ is N. Preferably, $X^1$ is N. Furthermore, it is preferred that $X^3$ is N. Furthermore, it is preferred that $X^2$ is $C(R^7)$ and $R^7$ is as defined above.

Preferred compounds of formula (I) as described above are those, wherein Y is a single bond, O, $N(R^9)C(O)$, $N(R^9)C(O)O$ or $N(R^9)SO_2$, and $R^9$ is as defined above. Preferably, Y is O or $N(R^9)C(O)O$, and $R^9$ is as defined above. Furthermore, it is preferred that Z is a single bond. Each of the groups given above for Y and Z respectively individually constitutes a preferred embodiment. The groups "Y" are on their left side bound to the $(CR^1R^2)_m$ moiety and on their right side to the $(CR^3R^4)_n$ moiety.

Another preferred embodiment of the present invention is concerned with compounds of formula (I), wherein $R^1$, $R^2$, $R^3$ and $R^4$ are hydrogen.

In another preferred embodiment of the present invention, $R^5$ is phenyl or naphthyl, which phenyl or naphthyl is optionally substituted with 1 to 3 substituents independently selected from the group consisting of halogen, lower-alkyl and lower-alkoxy. Preferably, $R^5$ is phenyl which is optionally substituted with 1 to 2 halogen. More preferably, $R^5$ is phenyl, 3-chloro-phenyl, 2,5-difluoro-phenyl or 3-chloro-4-fluoro-phenyl.

Other preferred compounds as defined above are those, wherein $R^6$ is hydrogen. Preferably, $R^7$ is hydrogen, halogen or lower-alkyl. It is furthermore preferred, that $R^7$ is hydrogen or halogen. More preferably, $R^7$ is hydrogen or chloro. In addition, it is preferred that $R^8$ is hydrogen. Compounds in which $R^9$ and $R^{10}$ are hydrogen are also preferred.

It is preferred that m is 1, 2 or 3. More preferably, m is 1. Furthermore, it is preferred that n is 0, 1, 2 or 3. More preferably, n is 1 or 2. Each of the individual values given above for m and n respectively, individually constitutes a preferred embodiment of the present invention, also in combination with any of the other preferred embodiments.

In particular, preferred compounds are the compounds of formula (I) described in the examples as individual compounds as well as pharmaceutically acceptable salts as well as pharmaceutically acceptable esters thereof. Preferred substituents are those of the specific examples given below.

Preferred compounds of formula (I) are those selected from the group consisting of:
2-(4-Phenyl-butyl)-3H-pyrimido[4,5-d]pyrimidin-4-one,
2-[2-(2,5-Difluoro-phenyl)-ethoxymethyl]-3H-pteridin-4-one,
2-[2-(3-Fluoro-phenyl)-ethoxymethyl]-3H-pyrimido[4,5-d]pyrimidin-4-one,
2-(2-m-Tolyl-ethoxymethyl)-3H-pyrimido[4,5-d]pyrimidin-4-one,
2-[2-(3-Chloro-4-fluoro-phenyl)-ethoxymethyl]-3H-pteridin-4-one,
3-Chloro-7-[2-(3-chloro-phenyl)-ethoxymethyl]-6H-pyrimido[4,5-c]pyridazin-5-one,
7-[2-(3-Chloro-phenyl)-ethoxymethyl]-6H-pyrimido[4,5-c]pyridazin-5-one,
7-[2-(3-Chloro-phenyl)-ethoxymethyl]-6H-pyrimido[5,4-e][1,2,4]triazin-5-one,
2-(2-Naphthalen-2-yl-ethoxymethyl)-3H-pteridin-4-one,
(4-Oxo-3,4-dihydro-pteridin-2-ylmethyl)-carbamic acid benzyl ester,
7-[2-(3-Chloro-4-fluoro-phenyl)-ethoxymethyl]-6H-pyrimido[4,5-c]pyridazin-5-one,
7-(2-Naphthalen-2-yl-ethoxymethyl)-6H-pyrimido[4,5-c]pyridazin-5-one,
7-(3-Phenyl-propyl)-6H-pyrimido[4,5-c]pyridazin-5-one,
7-(2-Benzyloxy-ethyl)-6H-pyrimido[4,5-c]pyridazin-5-one,
7-[2-(2-Fluoro-phenyl)-ethoxymethyl]-6H-pyrimido[4,5-c]pyridazin-5-one,
7-(3-Methoxy-phenoxymethyl)-6H-pyrimido[4,5-c]pyridazin-5-one,
N-(5-Oxo-5,6-dihydro-pyrimido[4,5-c]pyridazin-7-ylmethyl)-3-phenyl-propionamide,
(5-Oxo-5,6-dihydro-pyrimido[4,5-c]pyridazin-7-ylmethyl)-carbamic acid benzyl ester,
4-Methyl-N-[2-(5-oxo-5,6-dihydro-pyrimido[4,5-c]pyridazin-7-yl)-ethyl]-benzenesulfonamide,
N-(4-Oxo-3,4-dihydro-pyrimido[4,5-d]pyrimidin-2-ylmethyl)-3-phenyl-propionamide,
[2-(4-Oxo-3,4-dihydro-pyrimido[4,5-d]pyrimidin-2-yl)-ethyl]-carbamic acid benzyl ester,
2-Phenyl-ethanesulfonic acid (4-oxo-3,4-dihydro-pyrimido[4,5-d]pyrimidin-2-ylmethyl)-amide,
2-[2-(3-Chloro-phenyl)-ethyl]-3H-pteridin-4-one,
2-(3-Fluoro-phenyl)-N-(4-oxo-3,4-dihydro-pteridin-2-ylmethyl)-acetamide,
4-Methyl-N-[2-(4-oxo-3,4-dihydro-pteridin-2-yl)-ethyl]-benzenesulfonamide,
N-(4-Oxo-3,4-dihydro-pteridin-2-ylmethyl)-3-phenyl-propionamide,
2-[2-(3-Chloro-4-fluoro-phenyl)-ethoxymethyl]-6-ethyl-3H-pteridin-4-one,
and pharmaceutically acceptable salts and esters thereof.

Particularly preferred compounds of formula (I) are those selected from the group consisting of
2-(4-Phenyl-butyl)-3H-pyrimido[4,5-d]pyrimidin-4-one,
2-[2-(2,5-Difluoro-phenyl)-ethoxymethyl]-3H-pteridin-4-one,
2-[2-(3-Fluoro-phenyl)-ethoxymethyl]-3H-pyrimido[4,5-d]pyrimidin-4-one,
2-(2-m-Tolyl-ethoxymethyl)-3H-pyrimido[4,5-d]pyrimidin-4-one,
2-[2-(3-Chloro-4-fluoro-phenyl)-ethoxymethyl]-3H-pteridin-4-one,
3-Chloro-7-[2-(3-chloro-phenyl)-ethoxymethyl]-6H-pyrimido[4,5-c]pyridazin-5-one,
7-[2-(3-Chloro-phenyl)-ethoxymethyl]-6H-pyrimido[4,5-c]pyridazin-5-one,
7-[2-(3-Chloro-phenyl)-ethoxymethyl]-6H-pyrimido[5,4-e][1,2,4]triazin-5-one,
2-(2-Naphthalen-2-yl-ethoxymethyl)-3H-pteridin-4-one,
(4-Oxo-3,4-dihydro-pteridin-2-ylmethyl)-carbamic acid benzyl ester,
7-[2-(3-Chloro-4-fluoro-phenyl)-ethoxymethyl]-6H-pyrimido[4,5-c]pyridazin-5-one,
7-(2-Naphthalen-2-yl-ethoxymethyl)-6H-pyrimido[4,5-c]pyridazin-5-one,
and pharmaceutically acceptable salts and esters thereof.

More particularly preferred compounds of formula (I) are those selected from the group consisting of
2-[2-(2,5-Difluoro-phenyl)-ethoxymethyl]-3H-pteridin-4-one, 3-Chloro-7-[2-(3-chloro-phenyl)-ethoxymethyl]-6H-pyrimido[4,5-c]pyridazin-5-one,
7-[2-(3-Chloro-phenyl)-ethoxymethyl]-6H-pyrimido[4,5-c]pyridazin-5-one,
(4-Oxo-3,4-dihydro-pteridin-2-ylmethyl)-carbamic acid benzyl ester,
7-[2-(3-Chloro-4-fluoro-phenyl)-ethoxymethyl]-6H-pyrimido[4,5-c]pyridazin-5-one,
and pharmaceutically acceptable salts and esters thereof.

Other particularly preferred compounds of formula (I) are those selected from the group consisting of
7-(3-Phenyl-propyl)-6H-pyrimido[4,5-c]pyridazin-5-one,
7-(2-Benzyloxy-ethyl)-6H-pyrimido[4,5-c]pyridazin-5-one,
7-[2-(2-Fluoro-phenyl)-ethoxymethyl]-6H-pyrimido[4,5-c]pyridazin-5-one,
(5-Oxo-5,6-dihydro-pyrimido[4,5-c]pyridazin-7-ylmethyl)-carbamic acid benzyl ester,
N-(4-Oxo-3,4-dihydro-pyrimido[4,5-d]pyrimidin-2-ylmethyl)-3-phenyl-propionamide,
2-Phenyl-ethanesulfonic acid (4-oxo-3,4-dihydro-pyrimido[4,5-d]pyrimidin-2-ylmethyl)-amide,
7-[2-(2,5-Difluoro-phenyl)-ethoxymethyl]-5-methylene-5,6-dihydro-pyrimido[4,5-c]pyridazine,
2-[2-(3-Chloro-phenyl)-ethoxymethyl]-3H-pteridin-4-one,
and pharmaceutically acceptable salts and esters thereof.

Other more particularly preferred compounds of formula (I) are those selected from the group consisting of
(5-Oxo-5,6-dihydro-pyrimido[4,5-c]pyridazin-7-ylmethyl)-carbamic acid benzyl ester,
7-[2-(2,5-Difluoro-phenyl)-ethoxymethyl]-5-methylene-5,6-dihydro-pyrimido[4,5-c]pyridazine,
2-[2-(3-Chloro-phenyl)-ethoxymethyl]-3H-pteridin-4-one,
and pharmaceutically acceptable salts and esters thereof.

It will be appreciated that the compounds of general formula (I) in this invention may be derivatised at functional groups to provide derivatives which are capable of conversion back to the parent compound in vivo.

The invention further relates to a process for the manufacture of compounds of formula (I) as defined above, which process comprises converting a compound of formula (II)

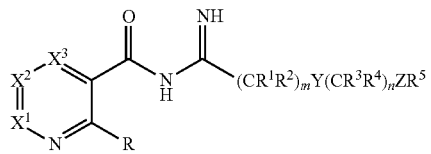

via an intramolecular condensation to the compound of formula (I), wherein R is F or Cl, $R^1$, $R^2$, $R^3$, $R^4$, $R^5$, $X^1$, $X^2$, $X^3$, Y, Z, m and n are as defined above.

The conversion of the compound of formula (II) to the compound of formula (I) via an intramolecular condensation can conveniently be carried out by methods known to the person skilled in the art, e.g. by treatment with a base like potassium tert-butylate or potassium carbonate in a solvent like DMSO or DMF at elevated temperatures up to reflux, to give the compounds of formula (I). Alternatively, for R=F cyclization to the final products (I) starting from aza 2-fluoro-3-pyridine carboxylic acids and amidines $H_2NC(NH)(CR^1R^2)_mY(CR^3R^4)_nZR^5$ can be achieved without isolation of acylamidines (II) by treating both starting materials e.g. with a base like N,N-diisopropyl ethyl amine in a solvent like acetonitrile at temperatures between ambient temperature and the reflux temperature of the solvent.

The present invention also relates to compounds of formula (I) as defined above, when prepared by a process as described above.

The compounds of formula (I), which are the subject of this invention, can be manufactured as outlined in Scheme A-C, by the methods given in the examples or by analogous methods. Unless otherwise indicated, $R^1$, $R^2$, $R^3$, $R^4$, $R^5$, $X^1$, $X^2$, $X^3$, Y, Z, m and n are as described above. The starting materials are either commercially available, described in the literature or can be prepared by methods well known in the art. In some instances, the syntheses require carboxylic acids as starting materials, which can be prepared as outlined in Schemes D-G.

Scheme A

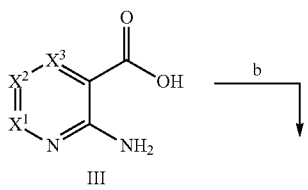

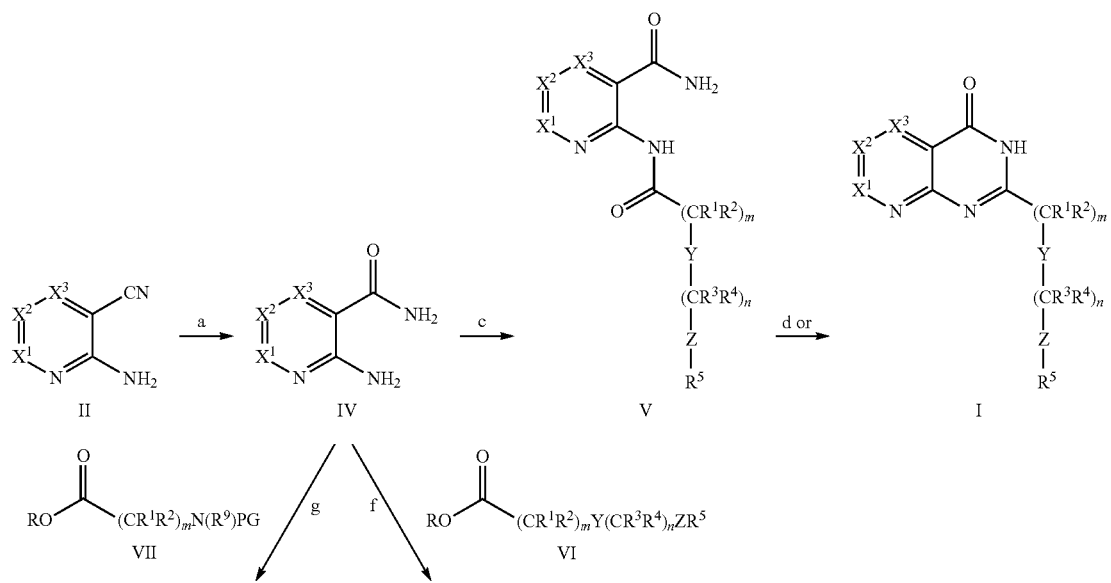
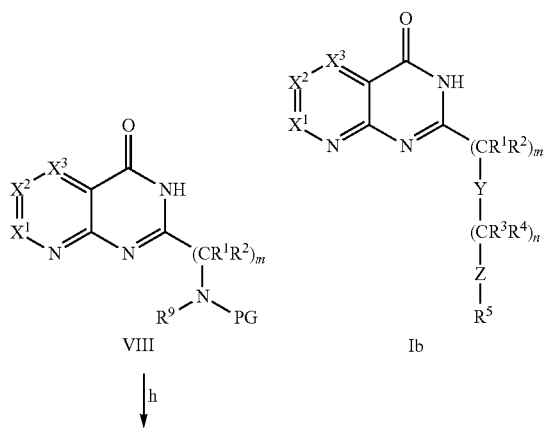
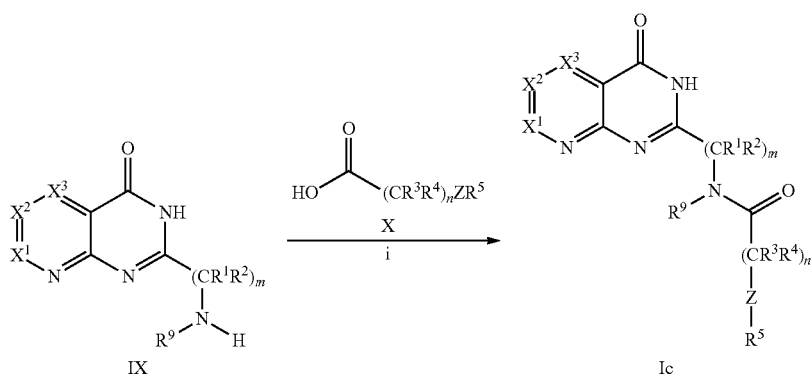

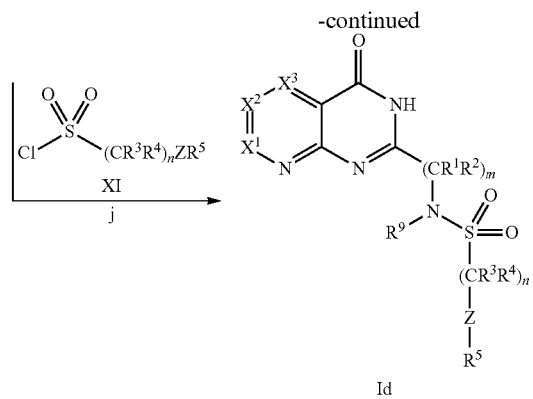

Aza 3H-pyrido[2,3-d]pyrimidin-4-ones (Ia) with an alkyl side chain (for m=1-3 or for m=0 and Y=single bond; $X^1$, $X^2$, $X^3$ are as described above) can be prepared by several methods. One method is outlined in scheme A. The starting materials of the general structure (II) or (III) are either commercially available, described in the literature or can be prepared by methods well known to a person skilled in the art. Amino-carboxylic acid amides (IV) can be prepared from compounds (II) by a hydrolysation step, for instance with a source of hydroxide ions, such as sodium or potassium hydroxide, and a catalyst, such as $H_2O_2$, in a suitable solvent, such as water, methanol or ethanol at elevated temperatures (step a). Alternatively, the amino-carboxylic acid amides (IV) might be prepared from the corresponding amino-carboxylic acids (III) by conversion to the corresponding acid chlorides with thionylchloride or oxalylchloride in solvents such as toluene or $CH_2Cl_2$ preferably under reflux conditions and subsequent treatment of the acid chlorides with $NH_4OH$ in solvents such as THF (step b). Amino-carboxylic acid amides (IV) can then be reacted with a suitably activated carboxylic acid, for instance with a carboxylic acid chloride, bromide or carboxylic anhydride, in a suitable solvent, such as THF, DMF or $CH_2Cl_2$ optionally in the presence of a base such as pyridine, DMAP, Huenig's base, triethylamine, $Na_2CO_3$ or ammonium hydroxide to give compounds with the general structure (V) which can be isolated after a usual workup including a purification step, such as column chromatography (step c). Activated carboxylic acids are either commercially available, described in the literature or can be prepared by methods well known to a person skilled in the art. (e.g. RCOCl: 1. $RCO_2H$, $CH_2Cl_2$, $(ClCO)_2$, DMF, rt; or 2. $RCO_2H$, thionyl chloride, reflux, with $R=(CR^1R^2)_m Y(CR^3R^4)_n ZR^5$). In a final step d, an intramolecular condensation can be carried out with compounds (V), for instance under basic conditions using bases such as sodium, potassium or cesium carbonate or sodium or potassium hydroxide in solvents such as ethanol, methanol, water or mixtures thereof at elevated temperatures up to reflux, to give aza 3H-pyrido[2,3-d]pyrimidin-4-ones (Ia) (step d). Alternatively, an acidic cyclization in the presence of p toluene sulfonic acid in a solvent such as toluene at elevated temperatures up to reflux can be employed (step e).

Aza 3H-pyrido[2,3-d]pyrimidin-4-ones (Ib) with an ether side chain (m≠0 and Y=O; $X^1$, $X^2$, $X^3$ are as described above) can be prepared by reacting amino-carboxylic acid amides (IV) with a carboxylic acid ester (VI) (R being e.g. Me, Et, Bn or another suited protecting group as described e.g. in "Protective Groups in Organic Chemistry" by T. W. Greene and P. G. M. Wutts, $2^{nd}$ Ed., 1991, Wiley N.Y.) in the presence of a base, for instance by treatment of a methyl ester (VI) (R=Me) with LiHMDS (lithium hexamethyldisilazide) in THF at ambient temperature (step f). Esters (VI) are either commercially available, described in the literature, can be prepared by methods described in schemes D)-G) (e.g. via esterifications of carboxylic acids (III) in scheme D) or carboxylic acids (V) in scheme E) by methods known in the art, compounds (IV) in scheme F) or compounds (III) in scheme G)) or by methods well known to a person skilled in the art. Aza 3H-pyrido[2,3-d]pyrimidin-4-ones (Ib) with an amine side chain (m≠0 and Y=NH; $X^1$, $X^2$, $X^3$ are as described above) can be prepared in close analogy to aza 3H-pyrido[2,3-d]pyrimidin-4-ones (Ib) with an ether side chain (m≠0 and Y=O; $X^1$, $X^2$, $X^3$ are as described above) (step f). To synthesize compounds (Ib) with Y equal to NH, carboxylic esters (VI) where Y is equal to NPG (PG=protecting group) have to be used in the cyclization step f. The protecting group can be removed after the aza pyrido pyrimidinone formation to form the final products (Ib) (Methods for the protection and deprotection of amines are well known to a person skilled in the art and described in the literature, e.g in "Protective Groups in Organic Chemistry" by T. W. Greene and P. G. M. Wutts, $2^{nd}$ Ed., 1991, Wiley N.Y.).

Protected amines (VIII) (m≠0, $R^9$ is either a residue as described above except for H or a protecting group) can be prepared from amino-carboxylic acid amides (IV) and carboxylic acid esters (VII) in close analogy to compounds (Ib) (step g). Alternatively, analogous acid chlorides $ClC(O)(CR^1R^2)_m N(R^9)PG$ can be reacted with amino-carboxylic acid amides (IV) as described in steps c)-e) to form compounds (VIII). Removal of the amine protecting group(s) yields amines (IX) ($R^9$ as described above) (step h). Methods for the protection and deprotection of amines are well known to a person skilled in the art and described in the literature, e.g in "Protective Groups in Organic Chemistry" by T. W. Greene and P. G. M. Wutts, $2^{nd}$ Ed., 1991, Wiley N.Y. For instance, phthalyl glycyl chloride can be reacted with a amino-carboxylic acid amides (IV) in the presence of a base like pyridine in a solvent like dichloromethane, preferably at temperatures between 0° C. and ambient temperature and subsequent treatment at elevated temperatures in a solvent like DMF in the presence of a base like ethyl-diisopropyl-amine to form cyclization products (VIII) with $R^9$ and PG together forming a phthalimide. Removal of the phthaloyl protecting group can for example be achieved by treatment with hydrazine in a solvent like ethanol preferably at elevated temperatures to form a primary amine (IX) ($R^9$=H). Esters (VII) and corresponding acid chlorides $ClC(O)(CR^1R^2)_m N(R^9)PG$ are either commercially available, described in the literature or can be prepared by methods well known to a person skilled in the art.

Amines (IX) can be condensed with suitably activated carboxylic acids (X) to form final products (Ic) (m≠0) (step i). Activated carboxylic acids are either commercially available, described in the literature or can be prepared by methods well known to a person skilled in the art. (e.g. carboxylic acid chlorides: 1. carboxylic acid, $CH_2Cl_2$, $(ClCO)_2$, DMF, rt; or 2. carboxylic acid, thionyl chloride, reflux). Alternatively, carboxylic acids (X) can be in situ activated and transformed into the final products (Ic) using e.g. N-(3-dimethylaminopropyl)-N'-ethyl-carbodiimide-hydrochloride, TBTU (O-(benzotriazol-1-yl)-N,N,N',N'-tetramethyluronium tetrafluoroborate) or BOP (benzotriazol-1-yloxytris(dimethylamino)phosphonium hexafluorophoshate) in the presence of a base such as ethyl-diisopropyl-amine, triethylamine, N-methylmorpholine optionally in the presence of 4-dimethylamino-pyridine or HOBt (1-hydroxybenzo-triazole) in solvents such as dichloromethane, DMF, DMA or dioxane at temperatures between 0° C. and ambient temperature. Condensation of amines (IX) with sulfonic acid chlorides (XI) gives the final products (Id) (m≠0) (step j). Sulfone amide formation can be carried out following methods described in the literature, e.g. reacting amine (IX) with sulfonic acid chloride (XI) in the presence of a base like ethyl-diisopropyl-amine in a solvent like dichloromethane preferably at temperatures between 0° C. and ambient temperature. Sulfonic acid chlorides are either commercially available, described in the literature or can be prepared by methods well known to a person skilled in the art. Alternatively, amines (IX) can be reacted with isocyanides to form final products (I) with X=NHC(O)NH as described in step g of scheme B or with chloroformates to form final products (I) with X=NHC(O)O as described in step h of scheme B.

If one of the starting materials, compounds of formula (IV), the activated carboxylic acid used to form compounds (V), esters (VI), esters (VII), carboxylic acids (X) or sulfonic acid chlorides (XI) contains one or more functional groups which are not stable or are reactive under the reaction conditions of one or more reaction steps, appropriate protecting groups (PG) (as described e.g. in "Protective Groups in Organic Chemistry" by T. W. Greene and P. G. M. Wutts, $2^{nd}$ Ed., 1991, Wiley N.Y.) can be introduced before the critical step applying methods well known in the art. Such protecting groups can be removed at a later stage of the synthesis using standard methods described in the literature.

If compounds (IV), esters (VI), esters (VII), carboxylic acids (X), sulfonic acid chlorides (XI) and/or the activated carboxylic acid used to form compounds (V) contain chiral centers, aza pyrido pyrimidinones (Ia), (Ib), (Ic) or (Id) can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization with optically pure acids or by separation of the antipodes by specific chromatographic methods using either a chiral adsorbens or a chiral eluent.

Scheme B

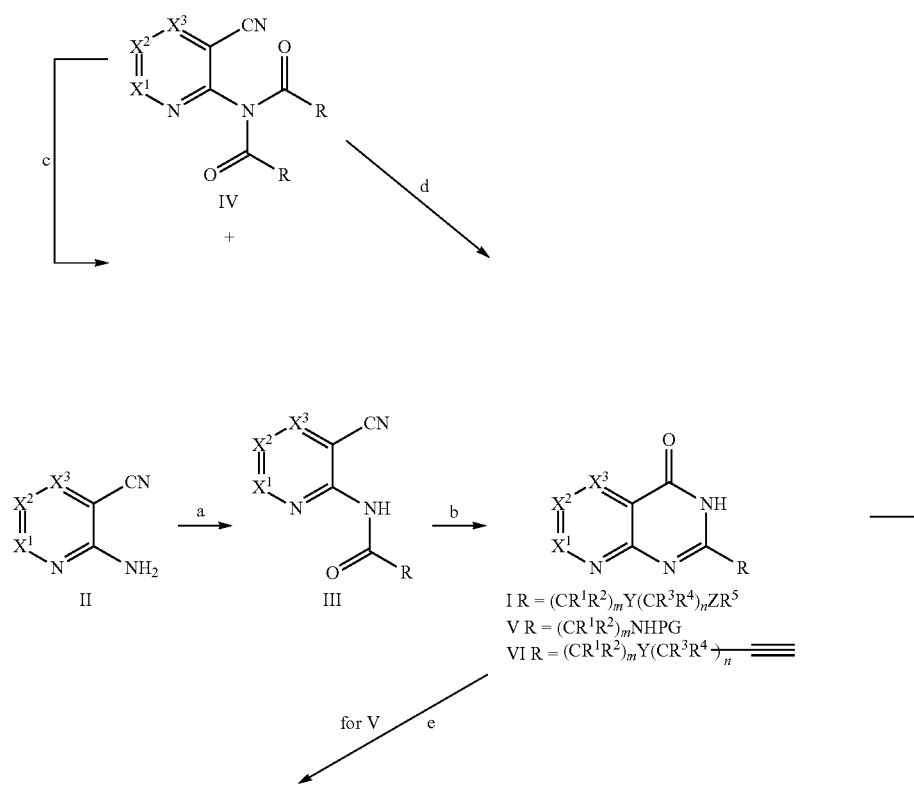

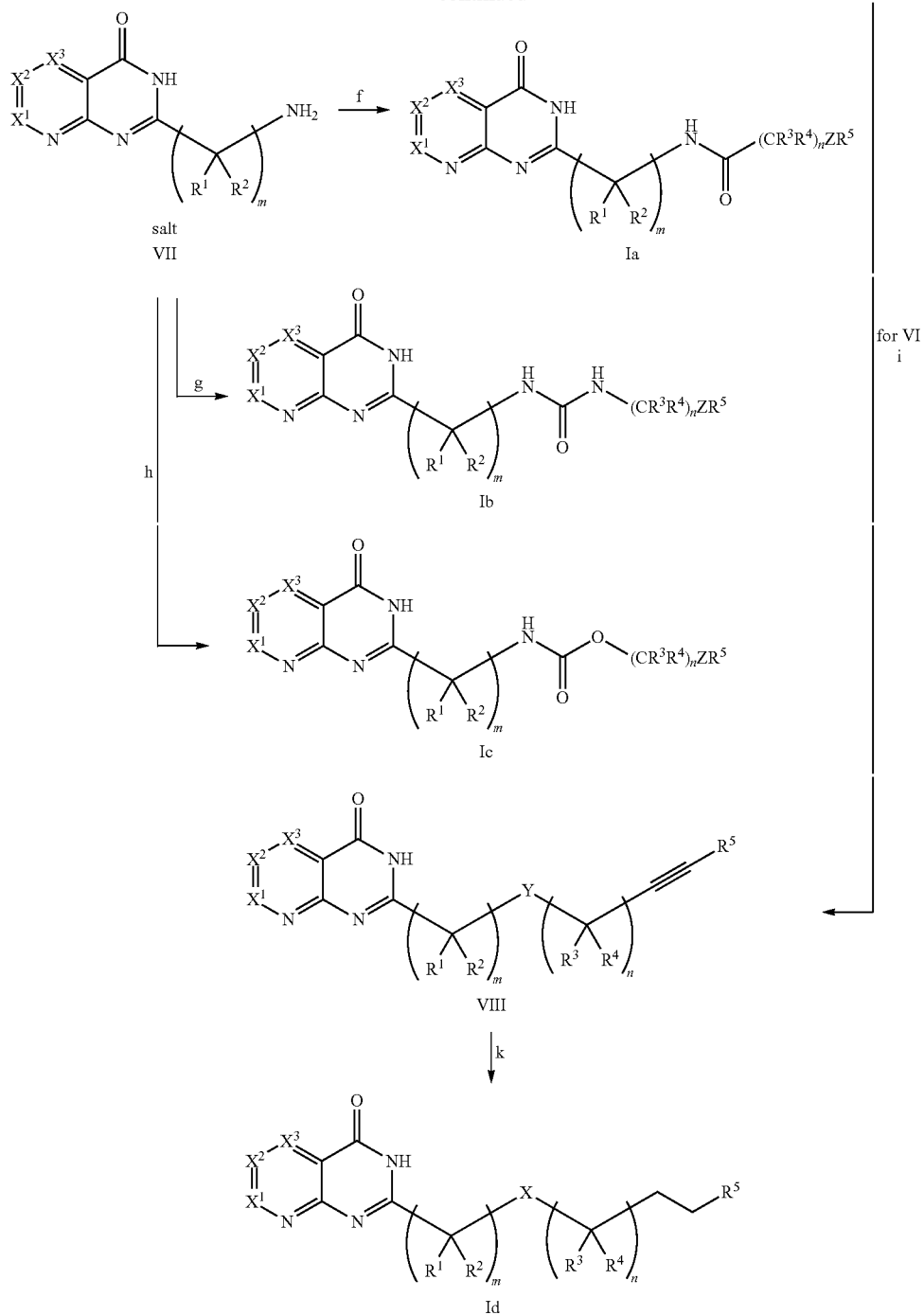

Another method to obtain aza 2-alkyl-3H-pyrido[2,3-d]pyrimidin-4-ones (I) (for m=1-3 or for m=0 and Y=single bond; $X^1$, $X^2$, $X^3$ are as described above) using amino-nitriles (II) as starting materials is outlined in Scheme B: Compounds (II) are reacted with a suitably activated carboxylic acid, for instance with a carboxylic acid chloride, bromide or carboxylic anhydride, in a suitable solvent, such as THF, DMF or $CH_2Cl_2$ optionally in the presence of a base such as pyridine, DMAP, Huenig's base, triethylamine, $Na_2CO_3$ or ammonium hydroxide to give N-acylated amino-nitriles (III) after the usual workup and purification (step a). In some cases the corresponding N,N-diacylated compounds (IV) can be isolated as well. Aza 2-alkyl-3H-pyrido[2,3-d]pyrimidin-4-ones (I) can be obtained from III by a hydrolysation of the nitrile functionality with a subsequent intramolecular condensation (step b). This reaction can be carried out by treatment of III with a source of hydroxide ions, such as sodium or potassium hydroxide or potassium carbonate, and a catalyst, such as $H_2O_2$, in a suitable solvent, such as water, methanol or ethanol at elevated temperatures. Compounds (IV) can be converted to the monoacylated amino-nitriles (III), for instance by using aqueous calcium carbonate as described in the literature (see e.g. B. Abarca et al. *Tetrahedron* 1989, 45, 7041-7048) (step c). Alternatively, aza 2-alkyl-3H-pyrido[2,3-d]pyrimidin-4-ones (I) might be prepared from compounds (IV) in a one pot sequence, by a selective mono-hydrolysis followed by a hydrolysation of the nitrile functionality with a subsequent intramolecular cyclization using sodium or potassium hydroxide or potassium carbonate, and a catalyst, such as $H_2O_2$, in a suitable solvent, such as water, methanol or ethanol at elevated temperatures (step d).

In the cases in which compounds of the general structure (V) or (VI) are isolated after the cyclization, these compounds can be modified further, optionally using one or more protecting groups which can be removed at an appropriate time point of the synthesis (steps e-k). Further modifications of derivatives (V) involve deprotection of the amine moiety to give amino derivatives (VII). The protecting group is removed under reaction conditions depending on the nature of the protecting group (step e). For instance, a benzyl carbamate can be removed under acidic conditions, for example by treatment with HBr/AcOH to provide amines (VII) as salts, which can serve as building blocks for further modifications. In the case of a BOC protecting group, the cleavage may be accomplished by treatment with TFA in $CH_2Cl_2$. VII can be transformed with a suitably activated carboxylic acid, for instance a carboxylic acid activated in situ by an activating agent such as EDCl optionally in the presence of HOBt and a base such as Huenig's base, $NEt_3$, NMM in $CH_2Cl_2$, DMF, DMA or dioxane, to aza 3H-pyrido[2,3-d]pyrimidin-4-ones (Ia), which can be obtained from the reaction mixture by a conventional workup (step f). Similarly, aza 3H-pyrido[2,3-d]pyrimidin-4-ones (Ib) can be obtained by reaction of VII with an isocyanide in solvents such as pyridine, dichloromethane at ambient temperatures up to reflux conditions (step g) followed by a conventional workup and purification. Aza 3H-pyrido[2,3-d]pyrimidin-4-ones (Ic) can be obtained from VII (step h) by treatment with a chloroformate and a base, such as triethylamine, NMM or Huenig's base, in a solvent such as dichloromethane, followed by a conventional workup and purification. Alternatively, amines (VII) can be condensed with sulfonic acid chlorides $ClSO_2(CR^3R^4)_nZR^5$ to yield aza 3H-pyrido[2,3-d]pyrimidin-4-ones (I) with Y=N($R^9$)$SO_2$ as described in step j of scheme A. Sulfonic acid chlorides $ClSO_2(CR^3R^4)_nZR^5$ are either commercially available, described in the literature or can be prepared by methods well known to a person skilled in the art. Sulfone amide formation can be carried out following methods described in the literature, e.g. reacting amine (VII) with sulfonic acid chloride $ClSO_2(CR^3R^4)_nZR^5$ in the presence of a base like ethyl-diisopropyl-amine in a solvent like dichloromethane preferably at temperatures between 0° C. and ambient temperature. If the 2-substituent is appropriately functionalized with a terminal acetylene motif as in derivatives (VI), Sonogashira reactions can be carried out according to literature-described procedures with halogenated aromatic reactants such as iodoarenes, bromoarenes or chloroarenes or with aromatic triflates (step i). The conditions of the Sonogashira reaction might involve a palladium catalyst and a copper catalyst such as $Pd(PPh_3)_4$/CuI or $Pd(OAc)_2$/CuI or $PdCl_2(PPh_3)_2$/CuI, and a base, for instance an amine such as triethylamine or piperidine, which might also serve as a solvent, alternatively a solvent such as THF might be used. After a conventional workup and purification, an acetylenic compound (VIII) is obtained. This can be further transformed (step k), by a reduction of the acetylenic bond under an atmosphere of hydrogen, with a catalyst such as palladium on charcoal in a solvent such as ethanol, to give aza 3H-pyrido[2,3-d]pyrimidin-4-ones (Id).

If one of the starting materials, compounds of formula (II) or the substituents introduced in steps g, h, f or i contain one or more functional groups which are not stable or are reactive under the reaction conditions, appropriate protecting groups (PG) (as described e.g. in "Protective Groups in Organic Chemistry" by T. W. Greene and P. G. M. Wutts, 2$^{nd}$ Ed., 1991, Wiley N.Y.) can be introduced before the critical step applying methods well known in the art. Such protecting groups can be removed at a later stage of the synthesis using standard methods described in the literature.

If compounds (III) or (IV) and/or the substituents introduced in steps g, h, f or i contain chiral centers, aza pyrido pyrimidinones (I), (Ia), (Ib), (Ic) or (Id) can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization with optically pure acids or by separation of the antipodes by specific chromatographic methods using either a chiral adsorbens or a chiral eluent.

Scheme C

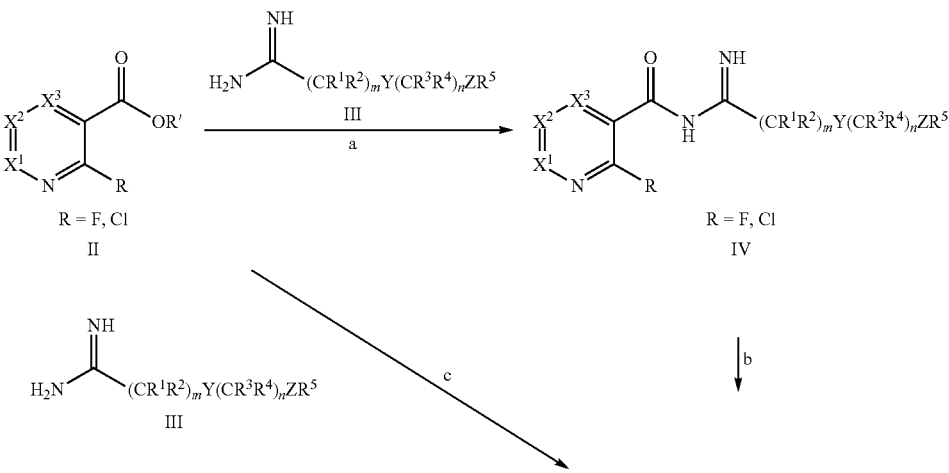

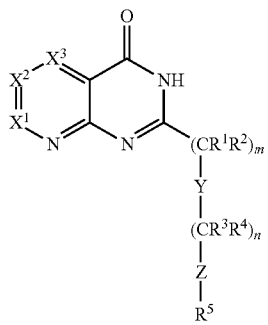

I

Aza 3H-pyrido[2,3-d]pyrimidin-4-ones (I) (for m=1-3 or for m=0 and Y=single bond; $X^1$, $X^2$, $X^3$ are as described above) can be synthesized starting from fluoro-carboxylic acids (II) (R'=H, R=F) or chloro-carboxylic acids (II) (R'=H, R=Cl) as outlined in scheme C: carboxylic acids (II) can be condensed—after suitable activation—with amidines (III) or the corresponding amidine salts to give acylamidines (IV) under reaction conditions well known to a person skilled in the art (step a). If the activated carboxylic acid is for instance a carboxylic acid chloride, bromide or carboxylic anhydride the reaction can be performed in a solvent such as dichloromethane, optionally in the presence of a base such as triethylamine, ethyl-diisopropyl-amine or N-ethylmorpholine at temperatures between 0° C. and ambient temperature. Activated carboxylic acids are either commercially available, described in the literature or can be prepared by methods well known to a person skilled in the art. (e.g. carboxylic acid chlorides: 1. carboxylic acid, $CH_2Cl_2$, $(ClCO)_2$, DMF, rt; or 2. carboxylic acid, thionyl chloride, reflux). Alternatively, carboxylic acids (II) can be in situ activated and transformed into acylamidines (IV) using e.g. N-(3-dimethylaminopropyl)-N'-ethyl-carbodiimide-hydrochloride, TBTU (O-(benzotriazol-1-yl)-N,N,N',N'-tetramethyluronium tetrafluoroborate) or BOP (benzotriazol-1-yloxytris(dimethylamino)phosphonium hexafluorophoshate) in the presence of a base such as ethyl-diisopropyl-amine, triethylamine, N-methylmorpholine optionally in the presence of 4-dimethylamino-pyridine or HOBt (1-hydroxybenzo-triazole) in solvents such as dichloromethane, DMF, DMA or dioxane preferably at temperatures between 0° C. and ambient temperature. Amidines (III) or its corresponding salts are either commercially available, described in the literature, or can be synthesized by methods well known to a person skilled in the art. For instance, compounds (III) can be synthesized by treating the corresponding carboxylic acid esters (e.g. compounds (IV) in scheme F) or compounds (III) in scheme G) or esters which can be synthesized via esterifications of carboxylic acids (III) in scheme D) or carboxylic acids (V) in scheme E by methods known in the art) with trimethylaluminum and ammonium chloride in a solvent like toluene, preferably at temperatures between 0° C. and ambient temperature. Cyclization of acylamidines (IV) to aza 3H-pyrido[2,3-d]pyrimidin-4-ones (I) can for example be achieved by treatment with a base like potassium tert-butylate or potassium carbonate in a solvent like DMSO or DMF at temperatures between 0° C. and the reflux temperature of the solvent (step b). In cases were fluoro-carboxylic acids (II) (R=F, R'=H) are used as starting materials, activated carboxylic acids and amidines (III) provide directly the final products (I) without prior isolation of acyl amidines (IV) (step c). Preferably, these reactions are performed by treating 2-fluoro substituted carboxylic acid chlorides and amidines (III) in the presence of a base like N,N-diisopropyl ethyl amine in a solvent like acetonitrile at temperatures between ambient temperature and the reflux temperature of the solvent. Aza 3H-pyrido[2,3-d]pyrimidin-4-ones (I) (for m=1-3 or for m=0 and Y=single bond; $X^1$, $X^2$, $X^3$ are as described above) can further be synthesized by condensing fluoro-carboxylic acid esters (II) (R'=alkyl, R=F) or chloro-carboxylic acid esters (II) (R'=alkyl, R=Cl) with amidines (III). Preferably, these reactions are performed in the presence of a base like potassium carbonate in a solvent like DMF at temperatures between 80° C. and the reflux temperature of the solvent (step c).

If one of the starting materials, compounds of formula (II) or (III) contain one or more functional groups which are not stable or are reactive under the reaction conditions, appropriate protecting groups (PG) (as described e.g. in "Protective Groups in Organic Chemistry" by T. W. Greene and P. G. M. Wutts, $2^{nd}$ Ed., 1991, Wiley N.Y.) can be introduced before the critical step applying methods well known in the art. Such protecting groups can be removed at a later stage of the synthesis using standard methods described in the literature. Optionally, aza 3H-pyrido[2,3-d]pyrimidin-4-ones carrying a protecting group can be further elaborated after the cyclization (step b or c) to the final products as described in schemes A and B.

If compounds (II) or (III) contain chiral centers, aza pyrido pyrimidinones (I) can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization with optically pure acids or by separation of the antipodes by specific chromatographic methods using either a chiral adsorbens or a chiral eluent.

Scheme D: Preparation of carboxylic acids used in Scheme A and B (1)

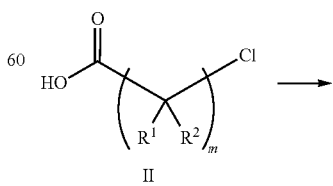

II

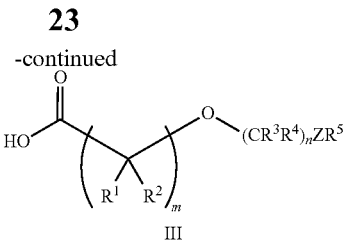

Alkoxyalkanoic acids (III) (with m≠0) can be prepared as outlined in scheme D: A chloroalkanoic acid (II) is reacted with an alcoholate in a suitable solvent, such as DMF, THF or mixtures thereof, typically at elevated temperature. The alcoholate may be pre-pared by treatment of the corresponding alcohol with a suitable base, such as NaH or KOtBu. After a workup that is suitable for weakly acidic organic substances, the alkoxyalkanoic acids (III) are usually obtained in a pure enough form to be used in the next step with no further purification.

Compounds (III) can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization with optically pure amines such as e.g. (R) or (S)-1-phenyl-ethylamine, (R) or (S)-1-naphthalen-1-yl-ethylamine, brucine, quinine or quinidine or by separation of the antipodes by specific chromatographic methods using either a chiral adsorbens or a chiral eluent. Optionally, compounds (III) can be synthesized in a stereoselective manner applying methods well known to a person skilled in the art.

Scheme E: Preparation of carboxylic acids used in Scheme A and B (2)

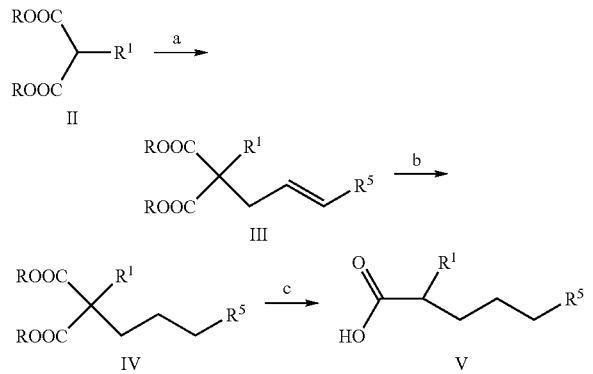

5-Aryl-pentanoic acids (V), which are substituted in the 2-position by hydrogen, an alkyl chain or a fluorinated alkyl chain, can be prepared by the method outlined in scheme E: In a first step a, deprotonated, suitably substituted malonate (II) (R being e.g. Me, Et, Bn or another suited protecting group as described e.g. in "Protective Groups in Organic Chemistry" by T. W. Greene and P. G. M. Wutts, $2^{nd}$ Ed., 1991, Wiley N.Y.) is reacted with triphenylphosphonium bromide and a (substituted) aryl aldehyde in a suitable solvent, such as DMF or DMSO, typically at elevated temperature. Substituted malonates (II) are easily obtained, either commercially or by well-known procedures, and are easily deprotonated by a suitable base, such as NaH, KOtBu, NaOMe or NaOEt, in a suitable solvent, such as diethyl ether or THF. The product (III) can be obtained from the reaction mixture by a usual workup including a purification step, for instance column chromatography. 2-Substituted 2-(3-aryl-allyl)-malonic acid esters (III) can be reduced to the corresponding 2-(3-arylpropyl)-malonic acid esters (IV) in a suitable solvent, such as methanol, ethanol or EtOAc, under an atmosphere of hydrogen, and with a suitable catalyst, such as palladium on charcoal (step b). Upon completion of the reaction, filtration and evaporation of the solvent might be sufficient to obtain the product (IV) in pure form. 2-Substituted 5-aryl-pentanoic acids (V) can be obtained from (IV) by a step commonly known as "saponification/decarboxylation" (step c): IV is heated together with an alkali hydroxide, such as potassium, sodium or lithium hydroxide in a suitable solvent, such as ethanol. Depending on the nature of R, a two step procedure: i) removal of the ester protecting group (as described e.g. in "Protective Groups in Organic Chemistry" by T. W. Greene and P. G. M. Wutts, $2^{nd}$ Ed., 1991, Wiley N.Y.) and ii) decarboxylation to give compounds (V) might be appropriate. After evaporation of the solvent, a workup that is suitable for weakly acidic organic substances, and a purification step, 2-substituted 5-aryl-pentanoic acids (V) are obtained from the reaction mixture.

Compounds (V) can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization with optically pure amines such as e.g. (R) or (S)-1-phenyl-ethylamine, (R) or (S)-1-naphthalen-1-yl-ethylamine, brucine, quinine or quinidine or by separation of the antipodes by specific chromatographic methods using either a chiral adsorbens or a chiral eluent. Optionally, compounds (V) can be synthesized in a stereoselective manner applying methods well known to a person skilled in the art.

Scheme F: Preparation of carboxylic acids used in Scheme A and B (3)

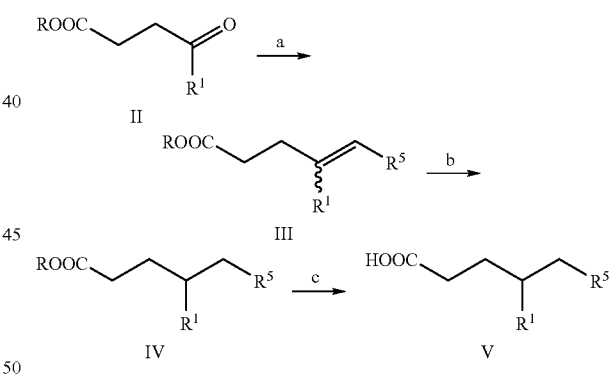

4-Alkyl or 4-fluoroalkyl-5-aryl-pentanoic acids (V) can be prepared as outlined in Scheme F: In a first step a, which is commonly known as a Wittig reaction, a suitable base such as KOtBu or sodium ethanolate is added to an aryl triphenyl phosphonium salt (Wittig salt) in a suitable solvent, such as ethanol or THF. The mixture is stirred for some time at a suitable temperature to allow for the formation of the well-known "ylide"-intermediate of the Wittig reaction, before ethyl levulinate or a similar, suitably substituted γ-ketoacid (II) is added to the mixture (R being e.g. Me, Et, Bn or another suited protecting group as described e.g. in "Protective Groups in Organic Chemistry" by T. W. Greene and P. G. M. Wutts, $2^{nd}$ Ed., 1991, Wiley N.Y.), and the mixture is kept at a temperature that is dependent on the nature of the employed Wittig reagent. III is obtained from the reaction mixture after the usual workup and a purification step, for instance column chromatography. In a next step b, the obtained alkenoic acid ester (III) can be reduced under an atmosphere of hydrogen, with a catalyst such as palladium on charcoal, in a solvent such as ethanol or EtOAc. Filtration and evaporation of the solvent might be sufficient to obtain the product (IV) in pure form. In a saponification step c, the obtained IV can be saponified with an alkali hydroxide in a suitable solvent, such as potassium, sodium or lithium hydroxide in solvents such as ethanol, methanol or THF or mixtures thereof, to give a 4-alkyl or a 4-fluoroalkyl-5-aryl-pentanoic acid (V) after a workup that is suitable for weakly acidic organic substances. Depending on the nature of R, an alternative procedure to cleave the ester (IV) might be appropriate (compare e.g. "Protective Groups in Organic Chemistry" by T. W. Greene and P. G. M. Wutts, $2^{nd}$ Ed., 1991, Wiley N.Y.).

Compounds (V) can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization with optically pure amines such as e.g. (R) or (S)-1-phenyl-ethylamine, (R) or (S)-1-naphthalen-1-yl-ethylamine, brucine, quinine or quinidine or by separation of the antipodes by specific chromatographic methods using either a chiral adsorbens or a chiral eluent. Optionally, compounds (V) can be synthesized in a stereoselective manner applying methods well known to a person skilled in the art.

Scheme G: Preparation of carboxylic acids used in Scheme A and B (4)

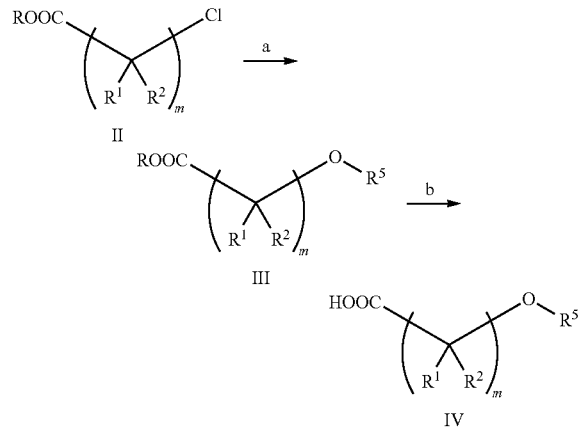

Aryloxy-alkanoic acids (IV) (with m≠0) can be prepared as outlined in Scheme G: In a first step a, a suitable base such as sodium ethanolate, sodium methanolate or KOtBu is added to a suitably substituted phenol and ethyl chloroalkanoate (II) in a solvent such as ethanol (R being e.g. Me, Et, Bn or another suited protecting group as described e.g. in "Protective Groups in Organic Chemistry" by T. W. Greene and P. G. M. Wutts, $2^{nd}$ Ed., 1991, Wiley N.Y.). After completion of the reaction, which might occur at elevated temperature, the mixture is worked up in the usual way. After evaporation of the solvent, a residue is obtained from which the product (III) can be isolated, for instance by column chromatography. In a next step b, the obtained aryloxy-alkanoic acid ester is saponified, for instance by treatment with an alkali hydroxide, such as potassium, sodium or lithium hydroxide, in a suitable solvent, such as ethanol, methanol or THF or mixtures thereof. A workup that is suitable for weakly acidic organic substances then gives aryloxy-alkanoic acids (IV). Depending on the nature of R, an alternative procedure to cleave the ester (III) might be appropriate (compare e.g. "Protective Groups in Organic Chemistry" by T. W. Greene and P. G. M. Wutts, $2^{nd}$ Ed., 1991, Wiley N.Y.).

Compounds (IV) can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization with optically pure amines such as e.g. (R) or (S)-1-phenyl-ethylamine, (R) or (S)-1-naphthalen-1-yl-ethylamine, brucine, quinine or quinidine or by separation of the antipodes by specific chromatographic methods using either a chiral adsorbens or a chiral eluent. Optionally, compounds (IV) can be synthesized in a stereoselective manner applying methods well known to a person skilled in the art.

The corresponding salts with acids can be obtained by standard methods known to the person skilled in the art, e.g. by dissolving the compound of formula (I) in a suitable solvent such as e.g. dioxan or THF and adding an appropriate amount of the corresponding acid. The products can usually be isolated by filtration or by chromatography. The conversion of a compound of formula (I) into a pharmaceutically acceptable salt with a base can be carried out by treatment of such a compound with such a base. One possible method to form such a salt is e.g. by addition of 1/n equivalents of a basic salt such as e.g. M(OH)$_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilization.

The conversion of compounds of formula (I) into pharmaceutically acceptable esters can be carried out e.g. by treatment of a suitable carboxy group present in the molecule with a suitable alcohol using e.g. a condensating reagent such as benzotriazol-1-yloxytris(dimethylamino)phosphonium hexafluorophosphate (BOP), N,N-dicylohexylcarbodiimide (DCC), N-(3-dimethylaminopropyl)-N'-ethylcarbodiimide hydrochloride (EDCl) or O-(1,2-dihydro-2-oxo-1-pyridyl)-N,N,N,N-tetra-methyluronium-tetrafluorborate (TBTU). Pharmaceutically acceptable esters can furthermore be prepared by treatment of a suitable hydroxy group present in the molecule with a suitable acid, optionally or if necessary in the presence of a condensating agent as described above.

Insofar as their preparation is not described in the examples, the compounds of formula (I) as well as all intermediate products can be prepared according to analogous methods or according to the methods set forth above. Starting materials are commercially available or known in the art.

As described above, the compounds of formula (I) of the present invention can be used in pharmaceutical compositions for the treatment and/or prevention of diseases which are modulated by HM74A agonists. Examples of such diseases are increased lipid and cholesterol levels, particularly dyslipidemia, low HDL-cholesterol, atherosclerotic diseases, hypertriglyceridemia, thrombosis, angina pectoris, peripheral vascular disease, stroke, diabetes, particularly non-insulin dependent diabetes mellitus, metabolic syndrome, Alzheimer's disease, Parkinson's disease, schizophrenia, sepsis, inflammatory diseases (such as e.g. asthma, arthritis, colitis, pancreatitis, cholestasis/fibrosis of the liver, and diseases that have an inflammatory component such as e.g. Alzheimer's disease or impaired/improvable cognitive function). The use as a pharmaceutical composition for the treatment of atherosclerosis, low HDL cholesterol levels, non-insulin dependent diabetes mellitus, and the metabolic syndrome is preferred.

The invention therefore also relates to pharmaceutical compositions comprising a compound as described above and a pharmaceutically acceptable carrier and/or adjuvant.

Further, the invention relates to compounds as described above for use as therapeutic active substances, especially as therapeutic active substances for the treatment and/or prevention of diseases which are modulated by HM74A agonists, particularly as therapeutically active substances for the treatment and/or prevention of increased lipid levels, increased cholesterol levels, atherosclerotic diseases, dyslipidemia, low HDL-cholesterol, hypertriglyceridemia, thrombosis, angina pectoris, peripheral vascular disease, stroke, diabetes, non-insulin dependent diabetes mellitus, metabolic syndrome, Alzheimer's disease, Parkinson's disease, schizophrenia, impaired or improvable cognitive function, sepsis, inflammatory diseases, asthma, arthritis, colitis, pancreatitis and cholestasis/fibrosis of the liver.

In another embodiment, the invention relates to a method for the treatment and/or prevention of diseases which are modulated by HM74A agonists, particularly for the treatment and/or prevention of increased lipid levels, increased cholesterol levels, atherosclerotic diseases, dyslipidemia, low HDL-cholesterol, hypertriglyceridemia, thrombosis, angina pectoris, peripheral vascular disease, stroke, diabetes, non-insulin dependent diabetes mellitus, metabolic syndrome, Alzheimer's disease, Parkinson's disease, schizophrenia, impaired or improvable cognitive function, sepsis, inflammatory diseases, asthma, arthritis, colitis, pancreatitis and cholestasis/fibrosis of the liver, which method comprises administering a compound as described above to a human or animal.

The invention further relates to the use of compounds as defined above for the treatment and/or prevention of diseases which are modulated by HM74A agonists, particularly for the treatment and/or prevention of increased lipid levels, increased cholesterol levels, atherosclerotic diseases, dyslipidemia, low HDL-cholesterol, hypertriglyceridemia, thrombosis, angina pectoris, peripheral vascular disease, stroke, diabetes, non-insulin dependent diabetes mellitus, metabolic syndrome, Alzheimer's disease, Parkinson's disease, schizophrenia, impaired or improvable cognitive function, sepsis, inflammatory diseases, asthma, arthritis, colitis, pancreatitis and cholestasis/fibrosis of the liver.

In addition, the invention relates to the use of compounds as described above for the preparation of pharmaceutical compositions for the treatment and/or prevention of diseases which are modulated by HM74A agonists, particularly for the treatment and/or prevention of increased lipid levels, increased cholesterol levels, atherosclerotic diseases, dyslipidemia, low HDL-cholesterol, hypertriglyceridemia, thrombosis, angina pectoris, peripheral vascular disease, stroke, diabetes, non-insulin dependent diabetes mellitus, metabolic syndrome, Alzheimer's disease, Parkinson's disease, schizophrenia, impaired or improvable cognitive function, sepsis, inflammatory diseases, asthma, arthritis, colitis, pancreatitis and cholestasis/fibrosis of the liver. Such pharmaceutical compositions comprise a compound as described above.

Prevention and/or treatment of atherosclerosis, low HDL cholesterol levels, non-insulin dependent diabetes mellitus, and the metabolic syndrome is preferred.

The following tests can be were carried out in order to determine the biological activity of the compounds of formula (I).

Primary Radiolabelled Ligand Competition Binding Assay

Nicotinic acid binding assays were performed with membrane preparations. A cell pellet containing $1 \times 10^8$ HEK-293 cells, stably transfected with the HM74A receptor, was resuspended in 3 ml of ice cold Dounce Buffer (10 mM Tris-Cl pH 7.6, 0.5 mM $MgCl_2$) supplemented with Roche protease inhibitor cocktail and homogenized at high speed on a Polytron homogenizer two times for 20 sec on ice. Nuclei and unbroken cells were removed by centrifugation for 5 min at 1,000×g after the addition of 1 ml of tonicity restoration buffer (10 mM Tris pH 7.6, 0.5 mM $MgCl_2$, 600 mM NaCl). The homogenate was centrifuged at 60,000×g for 30 min and pellets were resuspended in Tris buffer (50 mM Tris pH 7.4, containing protease inhibitors). Binding reactions contained 20 µg membranes as determined by BCA protein assay (Pierce), 50 nM [$^3$H]-nicotinic acid (Amersham) with or without compound addition in 250 µl of binding buffer (50 mM Tris pH 7.4, 2 mM $MgCl_2$, 0.02% CHAPS). Incubations were carried out at room temperature for 2 hrs and terminated by filtration using a Filtermate Harvester (PerkinElmer) onto GF/C filter plates (Millipore). Bound [$^3$H]-nicotinic acid was determined by scintillation counting using Top Count NXT (PerkinElmer). Compounds were dissolved in a concentration of $10^{-2}$ or $10^{-3}$ M in DMSO, further dilutions were performed in binding buffer. The effects of compounds were expressed as % inhibition of [$^3$H]-nicotinic acid binding. Sigmoidal curves were fitted using the XLfit3 program (ID Business Solutions Ltd. UK) and $IC_{50}$ values determined.

The compounds of the present invention exhibit $IC_{50}$ values in a range of about 0.001 µM to about 100 µM in the binding assay. Preferably, the compounds of the present invention have $IC_{50}$ values in a range of about 0.001 µM to about 10.0 µM, more preferably about 0.001 µM to about 1 µM.

Secondary Fluorescent Calcium Indicator Assay (FLIPR)

HEK-293 cells were grown in tissue culture medium (DMEM/Nut mix F12 Medium with Glutamax I (Invitrogen), containing 10% FBS) at 37° C. in a 5% $CO_2$ atmosphere. These cells were cultured in 6-well dishes at $3 \times 10^5$ cells/well and double transfected with DNA vectors (pcDNA3.1, Invitrogen) expressing either HM74A or HM74 and the chimeric G protein Gqi9. Two days after transfection the wells were combined and plated in 150 $cm^2$ flasks, in the presence of 50 µg/ml Hygromycin (Invitrogen) and 500 µg/ml Geneticin (Gibco). Fourteen days after plating, colonies were picked, expanded and analyzed for expression using a functional assay (FLIPR). Stable transfected HEK-293 cells expressing either HM74A or HM74 and the chimeric G protein Gqi9 were plated at 50,000 cells/well in black 96-well plates with clear bottom (Costar) and cultured to confluency overnight in growth media (DMEM/Nut mix F12 Medium with Glutamax I (Invitrogen), containing 10% FBS) at 37° C. in a humidified cell incubator containing 5% $CO_2$. Growth media was aspirated and replaced with 100 µl of 1×FLIPR Calcium Assay Dye (Molecular Devices) in Hank's balanced salt solution (HBSS) containing 10 mM HEPES, and 250 mM probenecid (Sigma), for 1 hour at 37° C. Cell plates were transferred to a FLIPR unit (Molecular Devices), and 50 µl of 3× compound dilution were added. Fluorescence emissions were measured and the effects of compounds were expressed as % stimulation of maximal nicotinic acid response (100 µM). Sigmoidal curves were fitted using the XLfit3 program (ID Business Solutions Ltd. UK) and $EC_{50}$ values determined.

The compounds of the present invention exhibit $EC_{50}$ values in a range of about 0.001 µM to about 100 µM in the FLIPR assay. Preferably, the compounds of the present invention have $EC_{50}$ values in a range of about 0.001 µM to about 10.0 µM; more preferably about 0.001 µM to about 1 µM.

In the following table, $IC_{50}$ values for some of the compounds of the present invention are shown.

| Example | IC$_{50}$ HM74A [μM] |
|---|---|
| 2 | 2.394 |
| 7 | 0.668 |

The compounds of formula I and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or suspensions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 5000 mg, preferably about 1 to 1000 mg, especially about 1 to 300 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1-1000 mg, preferably 1-300 mg, more preferably 1-100 mg, of a compound of formula I.

The following Examples serve to illustrate the present invention in more detail. They are, however, not intended to limit its scope in any manner.

EXAMPLES

Abbreviations

AcOH=acetic acid, CH$_2$Cl$_2$=dichloromethane, CH$_3$CN=acetonitrile, DIPEA=N,N-diisopropylethylamine, DMF=N,N-dimethylformamide, DMSO=dimethylsulfoxide, DMAP=N,N-dimethylaminopyridine, EDCl=N-(3-dimethylaminopropyl)-N'-ethylcarbodiimide hydrochloride, EtOAc=ethyl acetate, Et$_2$O=diethyl ether, h=hour, HCl=hydrochloric acid, HOBt=1-hydroxybenzo-triazole, KOtBu=potassium tert-butylate, MeOH=methanol, min=minutes, NaH=sodium hydride, Na$_2$SO$_4$=sodium sulfate, NMM=N-methylmorpholine, iPrOH=isopropanol, quant.=quantitative, TBME=tert-butylmethyl ether, TBTU=O-(benzotriazol-1-yl)-N,N,N',N'-tetramethyluronium tetrafluoroborate, THF=tetrahydrofuran, TFA=trifluoroacetic acid, MS=mass spectrometry, and NMR=Nuclear magnetic resonance.

Example 1

2-(4-Phenyl-butyl)-3H-pyrimido[4,5-d]pyrimidin-4-one 1.1

5-Phenyl-pentanoic acid (5-cyano-pyrimidin-4-yl)-amide

Under an atmosphere of nitrogen, oxalyl chloride (961 mg) was added dropwise to a solution of 5-phenylvaleric acid (Fluka, 1.00 g) in CH$_2$Cl$_2$ (8 ml) and DMF (0.4 ml). After stirring at ambient temperature overnight, the mixture was slowly added at 0° C. to a solution of 4-aminopyrimidine-5-carbonitrile (Aldrich, 505 mg) in pyridine (8 ml). The mixture was stirred overnight at r.t., taken up in CH$_2$Cl$_2$, washed with water, and dried (Na$_2$SO$_4$). After filtration, the solvent was evaporated, and the title compound (1.00 g, 64%) was obtained from the residue by column chromatography (silica gel, eluent gradient n-heptane/ethyl acetate=100:0-60:40). MS: m/e=281.3 [M+H$^+$]. $^1$H NMR (d$^6$-DMSO): δ 1.60-1.80 (m, 4H), 2.55-2.60 (m, 2H), 3.14 (t, 2H), 7.14-7.29 (m, 5H), 9.17 (d, 2H), 11.34 (bs, 1H).

1.2

2-(4-Phenyl-butyl)-3H-pyrimido[4,5-d]pyrimidin-4-one

Under an atmosphere of nitrogen, K$_2$CO$_3$ (3.057 g) was added to a solution of 5-phenyl-pentanoic acid (5-cyano-pyrimidin-4-yl)-amide (1.00 g) in MeOH (5 ml) and DMSO (1.2 ml). The mixture was cooled (ice bath) and hydrogen peroxide (35% in H$_2$O, 1.5 ml) was added dropwise. The mixture was taken up in ethyl acetate and washed with water. The organic layer was dried (Na$_2$SO$_4$), filtered, and the solvent was evaporated. 2-(4-Phenyl-butyl)-3H-pyrimido[4,5-d]pyrimidin-4-one (18 mg, 1.8%) was obtained from the residue by subsequent column chromatography (silica gel, eluent gradient n-heptan/ethyl acetate=100:0-60:40) and preparative, reverse-phase HPLC (Agilent Zorbax XdB C18 column, solvent gradient 5-95% CH$_3$CN in 0.1% TFA(aq) over 7 min, flow rate 30 ml/min). MS: m/e=279.3 [M−H$^-$]. $^1$H NMR (d$^6$-DMSO): δ 1.62-2.00 (m, 4H), 2.55-2.80 (m, 4H), 7.17-7.18 (m, 2H), 7.26-7.28 (m, 3H), 9.56 (d, 1H), 9.64 (d, 1H), 11.13 (bs, 1H).

Example 2

2-[2-(2,5-Difluoro-phenyl)-ethoxymethyl]-3H-pteridin-4-one

2.1
[2-(2,5-Difluoro-phenyl)-ethoxy]-acetic acid ethyl ester

Ethyl iodoacetate (340 μl, 2.9 mmol) was added to an ice cold solution of 2-(2,5-difluoro-phenyl)-ethanol (500 mg, 2.4 mmol), silver trifluoromethanesulfonate (685 mg, 2.7 mmol) and 2,6-di-tert-butylpyridin (820 μl, 3.6 mmol) in dichloromethane (5 ml). The reaction mixture was stirred at ambient temperature for 14 h, diluted with dichloromethane and filtered over speedex. Ice water/0.1 N aqueous HCl 1/1 was added to the filtrate and the filtrate was extracted two times with dichloromethane. The combined extracts were washed with aqueous $NaHCO_3$ solution and brine and dried over sodium sulfate. Removal of the solvent under reduced pressure left a colorless oil which was purified by column chromatography (silica gel, isopropyl acetate/heptane) to give the title compound (320 mg, 1.3 mmol; 54%) as colorless oil. MS: m/e=245.0 [M+H$^+$].

2.2
2-[2-(2,5-Difluoro-phenyl)-ethoxy]-acetamidine hydrochloride

A 2 M solution of trimethylaluminum in toluene (3.28 ml, 6.56 mmol) was added within 10 min to an ice cold suspension of dry ammonium chloride (350 mg, 6.54 mmol) in toluene (4 ml). The mixture was stirred for 1 h at ambient temperature. A solution of [2-(2,5-difluoro-phenyl)-ethoxy]-acetic acid ethyl ester (320 mg, 1.3 mmol) in toluene (2 ml) was added and the reaction mixture was warmed to 80° C. for 14 h. Cooling to 0° C. was followed by the careful addition of methanol (5 ml) and stirring for 30 min at ambient temperature. The solid was filtered off and washed with methanol. The filtrate was brought to dryness and treated with iPrOH/acetone 4/1 (12 ml) for 2 h. The solid was filtered off and the filtrate was brought to dryness to give the title compound (385 mg, 1.5 mmol; quant.) as yellow crystals. MS: m/e=215.4 [M+H$^+$].

2.3
3-Chloro-pyrazine-2-carboxylic acid{2-[2-(2,5-difluoro-phenyl)-ethoxy]-1-imino-ethyl}-amide 2-[2-(2,5-Difluoro-phenyl)-ethoxy]-acetamidine hydrochloride (158 mg, 0.631 mmol) was dissolved in DMF (3 ml) and 3-chloro-2-pyrazine-carboxylic acid (100 mg, 0.631 mmol), TBTU (213 mg, 0.662 mmol) and DIPEA (565 μl, 3.15 mmol) were added. The reaction mixture was stirred at ambient temperature for 4.5 h. Then water was added and the mixture was extracted three times with $CH_2Cl_2$. The combined organic extracts were washed with water and brine, dried ($Na_2SO_4$) and evaporated. The crude title compound (195 mg, brown gum) was used for the next reaction step without further purification. MS: m/e=355.2 [M+H$^+$].

2.4
2-[2-(2,5-Difluoro-phenyl)-ethoxymethyl]-3H-pteridin-4-one

Crude 3-chloro-pyrazine-2-carboxylic acid{2-[2-(2,5-difluoro-phenyl)-ethoxy]-1-imino-ethyl}-amide (190 mg) was dissolved in DMSO (1 ml). KOtBu (60 mg, 0.536 mmol) was added and the mixture was heated to 45° C. for 2.5 h. Then water was added, the pH was adjusted to 6 by addition of 0.1 N HCl and the resulting mixture was extracted three times with $CH_2Cl_2$. The combined extracts were washed with water (three times) and brine, dried ($Na_2SO_4$) and evaporated. The resulting orange brown solid was triturated with $Et_2O$. The remaining solid was filtered off, washed with a small amount of $Et_2O$ and dried to give the title compound as a light brown solid (40 mg, 23%). MS: m/e=319.1 [M+H$^+$].

Example 3

2-[2-(3-Fluoro-phenyl)-ethoxymethyl]-3H-pyrimido[4,5-d]pyrimidin-4-one

3.1
[2-(3-Fluoro-phenyl)-ethoxy]-acetic acid

To a solution of 2-(3-fluoro-phenyl)-ethanol (4.0 g, 28.5 mmol) in DMF (60 ml) was added sodium hydride (60% dispersion in oil, 2.40 g, 60 mmol). The suspension was heated to 60° C. for 0.75 hours before chloroacetic acid (4.72 g, 50 mmol) was added dropwise. After 36 hours at 60° C. the brown reaction mixture was brought to dryness under reduced pressure, dissolved in EtOAc and washed with 1M HCl, water and brine. The organic layers were dried ($MgSO_4$), filtered, the solvent was removed under reduced pressure and the residue was purified by column chromatography (silica gel, EtOAc/heptane 3:1) to yield the title compound (2.02 g, 18 mmol; 36%) as colorless liquid. MS: m/e=197.4 [M−H]$^-$.

3.2
[2-(3-fluoro-phenyl)-ethoxy]-acetic acid methyl ester

A solution of [2-(3-fluoro-phenyl)-ethoxy]-acetic acid (1.20 g, 6.05 mmol), EDCl (1.28 g, 6.66 mmol), HOBt (0.90 g, 6.66 mmol) and DIPEA (1.56 ml, 9.08 mmol) in methanol (4 ml) was stirred at 0° C. for 2 hours. The reaction mixture was brought to dryness, the residue was dissolved in $CH_2Cl_2$ and was washed twice with 1M NaOH and brine. The organic layers were dried over $MgSO_4$, filtered, the solvent was removed under reduced pressure and the residue was purified by column chromatography (silica gel, EtOAc/heptane, 1:4) to yield the title compound (1.20 g, 5.6 mmol; 93%) as colorless liquid. MS: m/e=213.2 [M+H]$^+$.

3.3
2-[2-(3-Fluoro-phenyl)-ethoxymethyl]-3H-pyrimido[4,5-d]pyrimidin-4-one A suspension of the commercially available 4-amino-5-pyrimidinecarboxamide [4786-51-0] (150 mg, 1.09 mmol) and of [2-(3-fluoro-phenyl)-ethoxy]-acetic acid methyl ester (254 mg, 1.19 mmol) in THF (7 ml) was treated with LiHMDS (1M solution in THF, 2.17 ml) and stirred overnight at ambient temperature. The resulting yellow suspension was filtered and the filtrate was evaporated to dryness and triturated with EtOAc/MeOH 9:1. The yellow solid was filtered off, the mother-liquid was evaporated and the remaining residue was purified by column chromatography (silica gel, EtOAc/MeOH, 9:1) to give the title compound as a white solid (3 mg, 1%), MS: m/e=301.1 [M+H$^+$].

Example 4

2-(2-m-Tolyl-ethoxymethyl)-3H-pyrimido[4,5-d]pyrimidin-4-one

In analogy to example 3.3, 4-amino-5-pyrimidinecarboxamide and (2-m-tolyl-ethoxy)-acetic acid methyl ester (prepared from 2-m-tolyl-ethanol [1875-89-4] in analogy to example 3.1-3.2) reacted in the presence of LiHMDS in THF to yield the title compound (after purification of the crude product with column chromatography (silica gel, EtOAc/MeOH) and crystallization from TBME) as white solid. MS: m/e=295.5 [M−H$^-$].

Example 5

2-[2-(3-Chloro-4-fluoro-phenyl)-ethoxymethyl]-3H-pteridin-4-one 5.1
[2-(3-Chloro-4-fluoro-phenyl)-ethoxy]-acetic acid ethyl ester In analogy to the procedure described in example 2.1, 2-(3-chloro-4-fluoro-phenyl)-ethanol was reacted with ethyl iodoacetate in the presence of silver trifluoromethanesulfonate and 2,6-di-tert-butylpyridin to give the title compound as colorless oil. MS: m/e=261.2 [M+H$^+$].

5.2
2-[2-(3-Chloro-4-fluoro-phenyl)-ethoxy]-acetamidine hydrochloride

In analogy to the procedure described in example 2.2, [2-(3-chloro-4-fluoro-phenyl)-ethoxy]-acetic acid ethyl ester was treated with trimethylaluminum and ammonium chloride to obtain the title compound as yellow crystals. MS: m/e=231.2 [M+H$^+$].

5.3
3-Chloro-pyrazine-2-carboxylic acid{2-[2-(3-chloro-4-fluoro-phenyl)-ethoxy]-1-imino-ethyl}-amide In analogy to the procedure described in 2.3, the crude title compound was obtained as a dark brown gum starting from 2-[2-(3-chloro-4-fluoro-phenyl)-ethoxy]-acetamidine hydrochloride and 3-chloro-2-pyrazine-carboxylic acid. MS: m/e=370.9 [M+H$^+$].

5.4
2-[2-(3-Chloro-4-fluoro-phenyl)-ethoxymethyl]-3H-pteridin-4-one

A mixture of crude 3-chloro-pyrazine-2-carboxylic acid{2-[2-(3-chloro-4-fluoro-phenyl)-ethoxy]-1-imino-ethyl}-amide (300 mg) and K$_2$CO$_3$ (223 mg, 1.616 mmol) in DMF (3 ml) was heated to 100° C. for 2 h. Then water was added and the pH was adjusted to 5 by addition of 0.1 N HCl. The brown precipitate that formed was filtered off, washed with water and dried. The resulting solid was triturated with Et$_2$O. The remaining solid was filtered off, washed with a small amount of Et$_2$O and dried to give the title compound as a light brown solid (122 mg, 45%). MS: m/e=335.2 [M+H$^+$].

Example 6

3-Chloro-7-[2-(3-chloro-phenyl)-ethoxymethyl]-6H-pyrimido[4,5-c]pyridazin-5-one 6.1
[2-(3-Chloro-phenyl)-ethoxy]-acetic acid methyl ester To a solution of 2-(3-chloro-phenyl)-ethanol (1.96 g, 12.51 mmol) in THF (55 ml) was added n-BuLi (8.8 ml, 1.6 M solution in hexane, 13.77 mmol) at −78° C. Then sodium iodoacetate (2.6 g, 12.51 mmol) was added and the mixture was allowed to warm to ambient temperature and was stirred overnight. The THF was then removed and 1 N HCl was added to the remaining residue to adjust the pH to 1. This mixture was extracted two times with dichloromethane and the combined extracts were dried (Na$_2$SO$_4$) and evaporated. The remaining red liquid was dissolved in MeOH (60 ml) and thionylchloride (1.56 ml, 21.5 mmol) was added dropwise at −15° C. The reaction mixture was then stirred for 1.5 h at ambient temperature. Then water was added and the mixture was extracted three times with ether. The combined extracts were washed with brine, dried (Na$_2$SO$_4$) and evaporated. The remaining residue was then purified by column chromatography (silica gel, heptane/ethyl acetate 95:5 to 88:12) to give the title compound (2.161 g, 9.45 mmol; 76%) as orange liquid. MS: m/e=229.2 [M+H$^+$].

6.2
2-[2-(3-Chloro-phenyl)-ethoxy]-acetamidine hydrochloride

In analogy to the procedure described in example 2.2, [2-(3-chloro-phenyl)-ethoxy]-acetic acid methyl ester was treated with trimethylaluminum and ammonium chloride to obtain the title compound as brown oil. MS: m/e=213.1 [M+H$^+$].

6.3
3,6-Dichloro-pyridazine-4-carboxylic acid{2-[2-(3-chloro-phenyl)-ethoxy]-1-imino-ethyl}-amide In analogy to the procedure described in 2.3, the crude title compound was obtained as a brown gum starting from 2-[2-(3-chloro-phenyl)-ethoxy]-acetamidine hydrochloride and 3,6-dichloro-pyridazine-4-carboxylic. MS: m/e=387.1 [M+H$^+$].

6.4
3-Chloro-7-[2-(3-chloro-phenyl)-ethoxymethyl]-6H-pyrimido[4,5-c]pyridazin-5-one A mixture of crude 3,6-dichloro-pyridazine-4-carboxylic acid{2-[2-(3-chloro-phenyl)-ethoxy]-1-imino-ethyl}-amide (170 mg) and K$_2$CO$_3$ (121 mg, 0.877 mmol) in DMF (2 ml) was heated to 100° C. for 2 h. Then water was added and the pH was adjusted to 2 by addition of 0.1 N HCl. The resulting mixture was extracted two times with CH$_2$Cl$_2$ and the combined extracts were washed with water and brine, dried (Na$_2$SO$_4$) and evaporated. The remaining residue was purified by column chromatography (silica gel, CH$_2$Cl$_2$/MeOH 100:0 to 98:2) to give the title compound as light yellow solid (1 mg, 0.5%). MS: m/e=351.1 [M+H$^+$].

Example 7

7-[2-(3-Chloro-phenyl)-ethoxymethyl]-6H-pyrimido[4,5-c]pyridazin-5-one 7.1
3-Oxo-2,3-dihydro-pyridazine-4-carbonitrile To a mixture of glyoxal bis(sodium hydrogen sulfite) monohydrate (25.24 g, 88.8 mmol) in water (80 ml) was added slowly a solution of cyanoacetohydrazide (8 g, 80.7 mmol) in ethanol/water 2:1 (120 ml). The mixture was then heated to 40° C. for 30 min. The pH was adjusted to 12-13 by addition of 10 N NaOH and stirring was continued for 3 h at 40° C. and for 1 h at 60° C. The reaction mixture was then allowed to cool to ambient temperature over night. The pH was then adjusted to 1-2 by addition of conc. HCl and the resulting mixture was evaporated. The remaining solid was extracted with CHCl$_3$ in a soxhlet-extractor for two days to obtain the title compound as a light brown solid (2.019 g, 16.67 mmol, 21%). $^1$H NMR (d$^6$-DMSO): 8.07 (d, J=4 Hz, 1H), 8.12 (d, J=4 Hz, 1H), 13.91 (s br, 1H).

7.2
3-Oxo-2,3-dihydro-pyridazine-4-carboxylic acid ethyl ester

3-Oxo-2,3-dihydro-pyridazine-4-carbonitrile (1 g, 8.26 mmol) was heated in a mixture of ethanol (2 ml) and conc. H$_2$SO$_4$ (1.1 ml) to 100° C. (oil-bath temperature) overnight. The reaction mixture was then allowed to cool to ambient temperature, poured onto ice and carefully neutralized with solid Na$_2$CO$_3$. The mixture was extracted three times with CHCl$_3$ and the combined extracts were dried (Na$_2$SO$_4$) and evaporated. The remaining residue was then purified by column chromatography (silica gel, heptane/ethyl acetate 70:30 to 35:65) to give the title compound (433 mg, 2.58 mmol; 31%) as white solid. MS: m/e=169.1 [M+H$^+$].

7.3

3-Chloro-pyridazine-4-carboxylic acid ethyl ester

A mixture of 3-oxo-2,3-dihydro-pyridazine-4-carboxylic acid ethyl ester (355 mg, 2.11 mmol) and POCl$_3$ (6 ml) was heated to 100° C. for 1 h. The volatiles were then removed and the remaining residue was neutralized with sat. NaHCO$_3$-solution. This mixture was extracted three times with Et$_2$O and the combined extracts were dried (Na$_2$SO$_4$) and evaporated to obtain the crude title compound. The remaining brown solid (364 mg, 1.95 mmol, 92%) was used in the next reaction step without further purification. MS: m/e=187.1 [M+H$^+$].

7.4

7-[2-(3-Chloro-phenyl)-ethoxymethyl]-6H-pyrimido[4,5-c]pyridazin-5-one

2-[2-(3-Chloro-phenyl)-ethoxy]-acetamidine hydrochloride (240 mg, 0.964 mmol; described in example 6.2) was dissolved in MeOH (2 ml) and NaOMe (30% solution in MeOH, 179 µl, 0.964 mmol) was added dropwise at 0° C. The suspension was stirred at ambient temperature for 15 min and then evaporated. To the remaining residue were added a solution of crude 3-chloro-pyridazine-4-carboxylic acid ethyl ester (180 mg) in DMF (3 ml) and subsequently K$_2$CO$_3$ (267 mg, 1.929 mmol) and the mixture was heated to 100° C. for 18 h. Then water was added, the pH was adjusted to 3 by addition of 0.1 N HCl and the mixture was extracted three times with CH$_2$Cl$_2$ and one time with ethyl acetate. The combined organic extracts were washed three times with diluted HCl (pH 3), dried (Na$_2$SO$_4$) and evaporated. The remaining residue was triturated with Et$_2$O and the brown solid was filtered off and further purified by column chromatography (silica gel, CH$_2$Cl$_2$/MeOH 95:5) to give the title compound (11 mg, 0.035 mmol; 3.6%) as brown solid. MS: m/e=317.1 [M+H$^+$].

Example 8

7-[2-(3-Chloro-phenyl)-ethoxymethyl]-6H-pyrimido[5,4-e][1,2,4]triazin-5-one 8.1

2-(Dimethylamino-methyleneamino)-malonic acid diethyl ester

A solution of NaOEt in ethanol was prepared by addition of sodium (532 mg, 23.2 mmol) to ethanol (29 ml) at 0° C. Then diethyl aminomalonate hydrochloride (5 g, 23.2 mmol) was added in one portion and the mixture was stirred at ambient temperature for 15 min. All volatiles were removed and benzene (24 ml) was added to the remaining residue. N,N-dimethylformamide dimethylacetal (4 ml, 29.9 mmol) was added, the reaction mixture was heated to reflux for 15 min and then stirred at ambient temperature over night. The mixture was then filtered through Celite and the filtrate was evaporated. Hexane/ethyl acetate 1:1 (10 ml) was added to the remaining residue and was removed again by evaporation. The crude title compound solidified in the freezer to give a yellow solid (4.767 g, 20.7 mmol, 89%). MS: m/e=231.1 [M+H$^+$].

8.2

6-Oxo-1,4,5,6-tetrahydro-[1,2,4]triazine-5-carboxylic acid ethyl ester 2-(Dimethylamino-methyleneamino)-malonic acid diethyl ester (1 g, 4.34 mmol) was dissolved in ethanol (6.5 ml) and the mixture was heated to 60° C. Hydrazine (1M solution in THF, 5.5 ml, 5.52 mmol) was added dropwise during a period of 30 min and the mixture was heated to reflux for another 30 min. The reaction mixture was then cooled to 0° C. for 1 h and the precipitate that formed was filtered off. The filtrate was evaporated and ethyl acetate/methanol 4:1 (16 ml) was added to the oily residue. The suspension that formed was again filtered and the filtrate was evaporated. The remaining residue was triturated with ethyl acetate (9 ml) and the light brown solid was filtered off. The filtrate was again evaporated, the remaining solid triturated with a small amount of ethyl acetate and the resulting light brown solid was filtered off and combined with the first batch to give the title compound (333 mg, 1.95 mmol, 45%). MS: m/e=172.1 [M+H$^+$].

8.3

6-Oxo-1,6-dihydro-[1,2,4]triazine-5-carboxylic acid ethyl ester

6-Oxo-1,4,5,6-tetrahydro-[1,2,4]triazine-5-carboxylic acid ethyl ester (329 mg, 1.92 mmol) was dissolved in ethanol (9 ml) and diacetoxyiodosobenzene (644 mg, 1.99 mmol) was added in one portion. After 2 h at ambient temperature all volatiles were removed and the remaining residue was purified by column chromatography (silica gel, heptane/ethyl acetate 70:30 to 50:50) to give the title compound (209 mg, 1.24 mmol; 64%) as yellow solid. MS: m/e=170.1 [M+H$^+$].

8.4

6-Chloro-[1,2,4]triazine-5-carboxylic acid ethyl ester

6-Oxo-1,6-dihydro-[1,2,4]triazine-5-carboxylic acid ethyl ester (115 mg, 0.68 mmol) in POCl$_3$ (1.5 ml) was heated to 100° C. for 2 h. All volatiles were then removed and the remaining residue was diluted with cold CHCl$_3$ and carefully neutralized with sat. NaHCO$_3$-solution. This mixture was extracted with cold CHCl$_3$. The organic phase was then washed with cold brine, dried (Na$_2$SO$_4$) and evaporated to give the crude title compound (115 mg, 90%) as brown gum, which was used in the next reaction step without further purification. MS: m/e=188.2 [M+H$^+$].

8.5

7-[2-(3-Chloro-phenyl)-ethoxymethyl]-6H-pyrimido[5,4-e][1,2,4]triazin-5-one

In analogy to the procedure described in 7.4, the title compound was obtained as a yellow solid starting from 2-[2-(3-chloro-phenyl)-ethoxy]-acetamidine hydrochloride and 6-chloro-[1,2,4]triazine-5-carboxylic acid ethyl ester. MS: m/e=318.1 [M+H$^+$].

Example 9

2-(2-Naphthalen-2-yl-ethoxymethyl)-3H-pteridin-4-one 9.1

(2-Naphthalen-2-yl-ethoxy)-acetic acid ethyl ester

In analogy to the procedure described in example 2.1, 2-naphthalen-2-yl-ethanol was reacted with ethyl iodoacetate in the presence of silver trifluoromethanesulfonate and 2,6-di-tert-butylpyridin to give the title compound as colorless oil. MS: m/e=259.3 [M+H$^+$].

9.2

2-(2-Naphthalen-2-yl-ethoxy)-acetamidine hydrochloride

In analogy to the procedure described in example 2.2, (2-naphthalen-2-yl-ethoxy)-acetic acid ethyl ester was treated with trimethylaluminum and ammonium chloride to obtain the title compound as off-white solid. MS: m/e=229.3 [M+H$^+$].

9.3

3-Chloro-pyrazine-2-carboxylic acid[1-imino-2-(2-naphthalen-2-yl-ethoxy)-ethyl]-amide Under an atmosphere of nitrogen, 3-chloro-2-pyrazinecarboxylic acid (Tyger, 250 mg), TBTU (532 mg), and diisopropylethylamine (1.34 ml) were added to a solution of 2-(2-naphthalen-2-yl-ethoxy)-acetamidine hydrochloride (417 mg) in DMF (5 ml). The reaction mixture was stirred for 2 h at r.t., diluted with dichloromethane and washed with water. The organic layer was dried (Na$_2$SO$_4$), filtered, and the solvent was evaporated. The obtained, crude title compound (567 mg) was used without further purification in the next step.

9.4

2-(2-Naphthalen-2-yl-ethoxymethyl)-3H-pteridin-4-one

K$_2$CO$_3$ (442 mg) was added to a solution of 3-chloro-pyrazine-2-carboxylic acid [1-imino-2-(2-naphthalen-2-yl-ethoxy)-ethyl]-amide (590 mg) in DMF (5 ml) and heated to 100° C. for 3 h. The reaction mixture was acidified to pH=5 (aqueous HCl, 1N) and extracted with ethyl acetate. The organic layers were dried (Na$_2$SO$_4$), filtered, and the solvent was evaporated. 2-(2-Naphthalen-2-yl-ethoxymethyl)-3H-pteridin-4-one (170 mg, 32%) was obtained from the residue by column chromatography (silica gel, eluent gradient n-heptane/ethyl acetate=80/20-50/50). MS: m/e=331.0 [M−H$^-$]. $^1$H NMR (d$^6$-DMSO): δ 3.09 (t, 2H), 3.91 (t, 2H), 4.51 (s, 2H), 7.45-7.50 (m, 3H), 7.79-7.88 (m, 4H), 8.82 (d, 1H), 8.99 (d, 2H), 12.72 (bs, 1H).

Example 10

(4-Oxo-3,4-dihydro-pteridin-2-ylmethyl)-carbamic acid benzyl ester 10.1

{2-[(3-Chloro-pyrazine-2-carbonyl)-amino]-2-imino-ethyl}-carbamic acid benzyl ester Under an atmosphere of nitrogen, 3-chloro-2-pyrazinecarboxylic acid (76 mg), TBTU (168 mg), and diisopropylethylamine (310 mg) were added to a solution of carbamimidoyl-methyl-carbamic acid benzyl ester [77390-81-9] (99 mg) in DMF (6 ml). The reaction mixture was stirred for 2 h at ambient temperature, diluted with dichloromethane and washed with water. The organic layer was dried (Na$_2$SO$_4$), filtered, and the solvent was evaporated. The obtained, crude title compound (220 mg) was used without further purification in the next step.

10.2

(4-Oxo-3,4-dihydro-pteridin-2-ylmethyl)-carbamic acid benzyl ester

K$_2$CO$_3$ (133 mg) was added to a solution of {2-[(3-chloro-pyrazine-2-carbonyl)-amino]-2-imino-ethyl}-carbamic acid benzyl ester (167 mg) in DMF (3 ml) and heated to 100° C. for 1.5 h. (4-Oxo-3,4-dihydro-pteridin-2-ylmethyl)-carbamic acid benzyl ester (16 mg, 11%) was obtained from the reaction mixture by preparative, reverse-phase HPLC (Agilent Zorbax XdB C18 column, solvent gradient 5-95% CH$_3$CN in 0.1% TFA(aq) over 7 min, flow rate 30 ml/min). MS: m/e=310.0 [M−H$^-$]

Example 11

7-[2-(3-Chloro-4-fluoro-phenyl)-ethoxymethyl]-6H-pyrimido[4,5-c]pyridazin-5-one 11.1

3-Chloro-pyridazine-4-carboxylic acid

To a solution of crude 3-chloro-pyridazine-4-carboxylic acid ethyl ester (565 mg) in THF (5 ml) was added 2N LiOH (3.03 ml, 6.06 mmol) and the mixture was stirred for 15 min at ambient temperature. The pH of the reaction mixture was then adjusted to 2 by addition of 0.1N HCl and the mixture was extracted five times with ethyl acetate. The combined extracts were dried (Na$_2$SO$_4$) and evaporated to give the crude title compound as a brown solid (452 mg, 94%) which was used in the next reaction step without further purification. $^1$H NMR (d$^6$-DMSO): 8.07 (d, J=5 Hz, 1H), 9.41 (d, J=5 Hz, 1H), 14.52 (s br, 1H).

11.2

3-Chloro-pyridazine-4-carboxylic acid{2-[2-(3-chloro-4-fluoro-phenyl)-ethoxy]-1-imino-ethyl}-amide In analogy to the procedure described in 2.3, the crude title compound was obtained as a brown oil starting from 2-[2-(3-chloro-4-fluoro-phenyl)-ethoxy]-acetamidine hydrochloride and 3-chloro-pyridazine-4-carboxylic acid. MS: m/e=371.0 [M+H$^+$].

11.3

7-[2-(3-Chloro-4-fluoro-phenyl)-ethoxymethyl]-6H-pyrimido[4,5-c]pyridazin-5-one

In analogy to the procedure described in 5.4, the title compound was obtained as an off-white solid starting from 3-chloro-pyridazine-4-carboxylic acid{2-[2-(3-chloro-4-fluoro-phenyl)-ethoxy]-1-imino-ethyl}-amide. MS: m/e=335.2 [M+H$^+$].

Example 12

7-(2-Naphthalen-2-yl-ethoxymethyl)-6H-pyrimido[4,5-c]pyridazin-5-one 12.1

3-Chloro-pyridazine-4-carboxylic acid[1-imino-2-(2-naphthalen-2-yl-ethoxy)-ethyl]-amide In analogy to the procedure described in 2.3, the crude title compound was obtained as a brown oil starting from 2-(2-naphthalen-2-yl-ethoxy)-acetamidine hydrochloride and 3-chloro-pyridazine-4-carboxylic acid. MS: m/e=369.2 [M+H$^+$].

12.2

7-(2-Naphthalen-2-yl-ethoxymethyl)-6H-pyrimido[4,5-c]pyridazin-5-one

In analogy to the procedure described in 5.4, the title compound was obtained as a white solid starting from 3-chloro-pyridazine-4-carboxylic acid[1-imino-2-(2-naphthalen-2-yl-ethoxy)-ethyl]-amide. MS: m/e=333.2 [M+H$^+$].

Example 13

7-(3-Phenyl-propyl)-6H-pyrimido[4,5-c]pyridazin-5-one 13.1

3-Chloro-pyridazine-4-carboxylic acid (1-imino-4-phenyl-butyl)-amide

In analogy to the procedure described in 2.3, the crude title compound was obtained as brown crystals starting from 4-phenyl-butyramidine hydrochloride (A. Zumbrunn, C. Lamberth, F. Schaub, Syn. Commun. (1998), 28(3), 475-483) and 3-chloro-pyridazine-4-carboxylic acid (example 11.1).

13.2

7-(3-Phenyl-propyl)-6H-pyrimido[4,5-c]pyridazin-5-one

In analogy to the procedure described in 5.4, the title compound was obtained as a brown solid starting from 3-chloro-pyridazine-4-carboxylic acid (1-imino-4-phenyl-butyl)-amide. MS: m/e=267.3 [M+H$^+$].

Example 14

7-(2-Benzyloxy-ethyl)-6H-pyrimido[4,5-c]pyridazin-5-one 14.1
3-Chloro-pyridazine-4-carboxylic acid (3-benzyloxy-1-imino-propyl)-amide In analogy to the procedure described in 2.3, the crude title compound was obtained as red oil starting from 3-benzyloxy-propionamidine hydrochloride [878774-08-4] and 3-chloro-pyridazine-4-carboxylic acid (example 11.1). MS: m/e=319.1 [M+H$^+$].

14.2
7-(2-Benzyloxy-ethyl)-6H-pyrimido[4,5-c]pyridazin-5-one

In analogy to the procedure described in 5.4, the title compound was obtained as green crystals starting from 3-chloro-pyridazine-4-carboxylic acid (3-benzyloxy-1-imino-propyl)-amide. MS: m/e=283.4 [M+H$^+$].

Example 15

7-[2-(2-Fluoro-phenyl)-ethoxymethyl]-6H-pyrimido[4,5-c]pyridazin-5-one 15.1
3-Chloro-pyridazine-4-carboxylic acid{2-[2-(2-fluoro-phenyl)-ethoxy]-1-imino-ethyl}-amide In analogy to the procedure described in 2.3, the crude title compound was obtained as orange oil starting from 2-[2-(2-fluoro-phenyl)-ethoxy]-acetamidine hydrochloride (2-[2-(2-fluoro-phenyl)-ethoxy]-acetamidine hydrochloride was prepared in analogy to 2-[2-(2,5-difluoro-phenyl)-ethoxy]-acetamidine hydrochloride (example 2.2) from 2-(2-fluoro-phenyl)-ethanol [50919-06-7]) and 3-chloro-pyridazine-4-carboxylic acid (example 11.1).

15.2
7-[2-(2-Fluoro-phenyl)-ethoxymethyl]-6H-pyrimido[4,5-c]pyridazin-5-one

In analogy to the procedure described in 5.4, the title compound was obtained as yellow crystals starting from 3-chloro-pyridazine-4-carboxylic acid{2-[2-(2-fluoro-phenyl)-ethoxy]-1-imino-ethyl}-amide. MS: m/e=301.1 [M+H$^+$].

Example 16

7-(3-Methoxy-phenoxymethyl)-6H-pyrimido[4,5-c]pyridazin-5-one 7-(3-Methoxy-phenoxymethyl)-6H-pyrimido[4,5-c]pyridazin-5-one can be prepared in analogy to 7-[2-(3-chloro-phenyl)-ethoxymethyl]-6H-pyrimido[4,5-c]pyridazin-5-one (example 7) from 3-chloro-pyridazine-4-carboxylic acid ethyl ester (example 7.3) and 2-(3-methoxy-phenoxy)-acetamidine hydrochloride [114986-37-7].

Example 17

N-(5-Oxo-5,6-dihydro-pyrimido[4,5-c]pyridazin-7-ylmethyl)-3-phenyl-propionamide N-(5-Oxo-5,6-dihydro-pyrimido[4,5-c]pyridazin-7-ylmethyl)-3-phenyl-propionamide can be prepared in analogy to 7-[2-(3-chloro-phenyl)-ethoxymethyl]-6H-pyrimido[4,5-c]pyridazin-5-one (example 7) from 3-chloro-pyridazine-4-carboxylic acid ethyl ester (example 7.3) and N-carbamimidoylmethyl-3-phenyl-propionamide hydrochloride (N-carbamimidoylmethyl-3-phenyl-propionamide hydrochloride can be prepared in analogy to 2-[2-(2,5-difluoro-phenyl)-ethoxy]-acetamidine hydrochloride (example 2.2) from (3-phenyl-propionylamino)-acetic acid ethyl ester [126861-97-0]).

Example 18

(5-Oxo-5,6-dihydro-pyrimido[4,5-c]pyridazin-7-ylmethyl)-carbamic acid benzyl ester 18.1
{2-[(3-Chloro-pyridazine-4-carbonyl)-amino]-2-imino-ethyl}-carbamic acid benzyl ester In analogy to the procedure described in 2.3, the crude title compound was obtained as orange crystals starting from carbamimidoylmethyl-carbamic acid benzyl ester hydrochloride [50850-19-6] and 3-chloro-pyridazine-4-carboxylic acid (example 11.1). MS: m/e=348.1 [M+H$^+$].

18.2
(5-Oxo-5,6-dihydro-pyrimido[4,5-c]pyridazin-7-ylmethyl)-carbamic acid benzyl ester In analogy to the procedure described in 5.4, the title compound was obtained as colorless oil starting from {2-[(3-chloro-pyridazine-4-carbonyl)-amino]-2-imino-ethyl}-carbamic acid benzyl ester. MS: m/e=310.0 [M−H$^-$].

Example 19

4-Methyl-N-[2-(5-oxo-5,6-dihydro-pyrimido[4,5-c]pyridazin-7-yl)-ethyl]-benzenesulfonamide 4-Methyl-N-[2-(5-oxo-5,6-dihydro-pyrimido[4,5-c]pyridazin-7-yl)-ethyl]-benzenesulfonamide can be prepared in analogy to 7-[2-(3-chloro-phenyl)-ethoxymethyl]-6H-pyrimido[4,5-c]pyridazin-5-one (example 7) from 3-chloro-pyridazine-4-carboxylic acid ethyl ester (example 7.3) and 3-(toluene-4-sulfonylamino)-propionamidine hydrochloride [4349-34-2].

Example 20

N-(4-Oxo-3,4-dihydro-pyrimido[4,5-d]pyrimidin-2-ylmethyl)-3-phenyl-propionamide 20.1
4-[2-(1,3-Dioxo-1,3-dihydro-isoindol-2-yl)-acetylamino]-pyrimidine-5-carboxylic acid amide To a solution of 4-amino-pyrimidine-5-carboxylic acid amide [4786-51-0] (300 mg, 2.17 mmol) in THF 10 (mL) and DIPEA (0.56 mL, 3.26 mmol), was added phthalyl-glycyl-chloride (534 mg, 2.39 mmol) at 0° C. The reaction mixture was stirred one hour, evaporated to dryness and triturated with CH$_2$Cl$_2$/EtOAc (1/1). Filtration delivered 4-[2-(1,3-dioxo-1,3-dihydro-isoindol-2-yl)-acetylamino]-pyrimidine-5-carboxylic acid amide as a light yellow solid (108 mg, 15%). MS (m/e): 326.1 [M+H$^+$].

20.2
2-(4-Oxo-3,4-dihydro-pyrimido[4,5-d]pyrimidin-2-ylmethyl)-isoindole-1,3-dione 4-[2-(1,3-Dioxo-1,3-dihydro-isoindol-2-yl)-acetylamino]-pyrimidine-5-carboxylic acid amide (100 mg, 0.31 mmol) in DMF (2 mL) was treated with DIPEA (0.39 mL, 2.29 mmol) for 2 hours at 90° C. The reaction mixture was evaporated, the residue was triturated with EtOAc and filtrated to yield 2-(4-oxo-3,4-dihydro-pyrimido[4,5-d]pyrimi-

20.3

2-Aminomethyl-3H-pyrimido[4,5-d]pyrimidin-4-one

A suspension of 2-(4-oxo-3,4-dihydro-pyrimido[4,5-d]pyrimidin-2-ylmethyl)-isoindole-1,3-dione (50 mg, 0.163 mmol) and hydrazine monohydrate (0.25 mL, 5.09 mmol) in ethanol (3 mL) was stirred at ambient temperature for 4 hours. A light yellow solid of 2-amino-isoindole-1.3-dione was filtered off, the filtrate was evaporated and purified by column chromatography (silica gel, EtOAc/MeOH, 1/1) to yield 2-aminomethyl-3H-pyrimido[4,5-d]pyrimidin-4-one (24 mg, 83%) as a off-white solid. MS (m/e): 176.2 [M–H$^-$].

20.4

N-(4-oxo-3,4-dihydro-pyrimido[4,5-d]pyrimidin-2-ylmethyl)-3-phenyl-propionamide

To a suspension of 2-aminomethyl-3H-pyrimido[4,5-d]pyrimidin-4-one (12 mg, 0.068 mmol) in THF (0.2 mL) and DIPEA (0.050 mL, 0.29 mmol) was added 3-phenyl-propionyl chloride (14 mg, 0.08 mmol) at ambient temperature. The reaction mixture was stirred one hour, evaporated and purified by column chromatography (silica gel, EtOAc/MeOH, 1/1) to yield N-(4-oxo-3,4-dihydro-pyrimido[4,5-d]pyrimidin-2-ylmethyl)-3-phenyl-propionamide as a white solid (0.8 mg, 3.8%). MS (m/e): 310.3 [M+H$^+$].

Example 21

[2-(4-Oxo-3,4-dihydro-pyrimido[4,5-d]pyrimidin-2-yl)-ethyl]-carbamic acid benzyl ester

[2-(4-Oxo-3,4-dihydro-pyrimido[4,5-d]pyrimidin-2-yl)-ethyl]-carbamic acid benzyl ester can be prepared in analogy to 2-(4-phenyl-butyl)-3H-pyrimido[4,5-d]pyrimidin-4-one (example 1) from 4-aminopyrimidine-5-carbonitrile and 3-benzyloxycarbonylamino-propionic acid [2304-94-1].

Example 22

2-Phenyl-ethanesulfonic acid (4-oxo-3,4-dihydro-pyrimido[4,5-d]pyrimidin-2-ylmethyl)-amide

In analogy to the procedure described in example 20.4, 2-aminomethyl-3H-pyrimido[4,5-d]pyrimidin-4-one (example 20.3) was treated with 2-phenyl-ethanesulfonyl chloride [4025-71-2] to obtain 2-phenyl-ethanesulfonic acid (4-oxo-3,4-dihydro-pyrimido[4,5-d]pyrimidin-2-ylmethyl)-amide as light brown solid. MS: m/e=346.3 [M+H$^+$].

Example 23

2-[2-(3-Chloro-phenyl)-ethyl]-3H-pteridin-4-one

2-[2-(3-Chloro-phenyl)-ethyl]-3H-pteridin-4-one can be prepared in analogy to 2-[2-(2,5-difluoro-phenyl)-ethoxymethyl]-3H-pteridin-4-one (example 2) from 3-chloro-2-pyrazine-carboxylic acid and 3-(3-chloro-phenyl)-propionamidine hydrochloride (3-(3-chloro-phenyl)-propionamidine hydrochloride can be prepared in analogy to 2-[2-(2,5-difluoro-phenyl)-ethoxy]-acetamidine hydrochloride (example 2.2) from 3-(3-chloro-phenyl)-propionic acid ethyl ester [7116-35-0]).

Example 24

2-(3-Fluoro-phenyl)-N-(4-oxo-3,4-dihydro-pteridin-2-ylmethyl)-acetamide

2-(3-Fluoro-phenyl)-N-(4-oxo-3,4-dihydro-pteridin-2-ylmethyl)-acetamide can be prepared in analogy to 2-[2-(2,5-difluoro-phenyl)-ethoxymethyl]-3H-pteridin-4-one (example 2) from 3-chloro-2-pyrazine-carboxylic acid and N-carbamimidoylmethyl-2-(3-fluoro-phenyl)-acetamide hydrochloride (N-carbamimidoylmethyl-2-(3-fluoro-phenyl)-acetamide hydrochloride can be prepared in analogy to 2-[2-(2,5-difluoro-phenyl)-ethoxy]-acetamidine hydrochloride (example 2.2) from [2-(3-fluoro-phenyl)-acetylamino]-acetic acid ethyl ester which can be prepared from (3-fluoro-phenyl)-acetic acid [331-25-9] and amino-acetic acid ethyl ester [459-73-4] using typical amide bond formation conditions as e.g. described in step i of scheme A).

Example 25

4-Methyl-N-[2-(4-oxo-3,4-dihydro-pteridin-2-yl)-ethyl]-benzenesulfonamide

4-Methyl-N-[2-(4-oxo-3,4-dihydro-pteridin-2-yl)-ethyl]-benzenesulfonamide can be prepared in analogy to 2-[2-(2,5-difluoro-phenyl)-ethoxymethyl]-3H-pteridin-4-one (example 2) from 3-chloro-2-pyrazine-carboxylic acid and 3-(toluene-4-sulfonylamino)-propionamidine hydrochloride [4349-34-2].

Example 26

N-(4-Oxo-3,4-dihydro-pteridin-2-ylmethyl)-3-phenyl-propionamide

N-(4-Oxo-3,4-dihydro-pteridin-2-ylmethyl)-3-phenyl-propionamide can be prepared in analogy to 2-[2-(2,5-difluoro-phenyl)-ethoxymethyl]-3H-pteridin-4-one (example 2) from 3-chloro-2-pyrazine-carboxylic acid and N-carbamimidoylmethyl-3-phenyl-propionamide hydrochloride (N-carbamimidoylmethyl-3-phenyl-propionamide hydrochloride can be prepared in analogy to 2-[2-(2,5-difluoro-phenyl)-ethoxy]-acetamidine hydrochloride (example 2.2) from (3-phenyl-propionylamino)-acetic acid ethyl ester [126861-97-0]).

Example 27

2-[2-(3-Chloro-4-fluoro-phenyl)-ethoxymethyl]-6-ethyl-3H-pteridin-4-one

2-[2-(3-Chloro-4-fluoro-phenyl)-ethoxymethyl]-6-ethyl-3H-pteridin-4-one can be prepared as described in step f of scheme A from 3-chloro-6-ethyl-pyrazine-2-carboxylic acid (which can be prepared e.g. from 3-amino-6-bromo-pyrazine-2-carboxylic acid methyl ester [6966-01-4] using methods which are known to a person skilled in the art, e.g. via sequentional treatment with i) ethynyl-trimethyl-silane; ii) tetra-n-butylammonium fluoride; iii) hydrogen using palladium on charcoal as a catalyst; iv) conversion of the ester to the primary amide using e.g. NH$_3$) and [2-(3-chloro-4-fluoro-phenyl)-ethoxy]-acetic acid ethyl ester (example 5.2).

Example 28

7-[2-(2,5-Difluoro-phenyl)-ethoxymethyl]-5-methylene-5,6-dihydro-pyrimido[4,5-c]pyridazine

28.1

3-Chloro-pyridazine-4-carboxylic acid{2-[2-(2,5-difluoro-phenyl)-ethoxy]-1-imino-ethyl}-amide

In analogy to the procedure described in 2.3, the crude title compound was obtained as orange oil starting from 2-[2-(2, 5-difluoro-phenyl)-ethoxy]-acetamidine hydrochloride (example 2.2) and 3-chloro-pyridazine-4-carboxylic acid (example 11.1).

28.2
7-[2-(2,5-Difluoro-phenyl)-ethoxymethyl]-5-methylene-5,6-dihydro-pyrimido[4,5-c]pyridazine In analogy to the procedure described in 5.4, the title compound was obtained as brown crystals starting from 3-chloro-pyridazine-4-carboxylic acid{2-[2-(2,5-difluoro-phenyl)-ethoxy]-1-imino-ethyl}-amide. MS: m/e=319.1 [M+H$^+$].

Example 29

2-[2-(3-Chloro-phenyl)-ethoxymethyl]-3H-pteridin-4-one 29.1
3-Chloro-pyrazine-2-carboxylic acid{2-[2-(3-chloro-phenyl)-ethoxy]-1-imino-ethyl}-amide In analogy to the procedure described in 2.3, the crude title compound was obtained as orange brown oil starting from 2-[2-(3-chloro-phenyl)-ethoxy]-acetamidine hydrochloride (example 6.2) and 3-chloro-2-pyrazine-carboxylic acid. MS: m/e=353.1 [M+H$^+$].

29.2
2-[2-(3-Chloro-phenyl)-ethoxymethyl]-3H-pteridin-4-one

In analogy to the procedure described in 2.4, the title compound was obtained as light brown solid starting from 3-chloro-pyrazine-2-carboxylic acid{2-[2-(3-chloro-phenyl)-ethoxy]-1-imino-ethyl}-amide. MS: m/e=317.1 [M+H$^+$].

Example A

Film coated tablets containing the following ingredients can be manufactured in a conventional manner:

| Ingredients | Per tablet | |
| --- | --- | --- |
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxyde (yellow) | 0.8 mg | 1.6 mg |
| Titan dioxide | 0.8 mg | 1.6 mg |

The active ingredient is sieved and mixed with microcristalline cellulose and the mixture is granulated with a solution of polyvinylpyrrolidon in water. The granulate is mixed with sodium starch glycolate and magnesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
| --- | --- |
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
| --- | --- |
| Compound of formula (I) | 3.0 mg |
| Polyethylene Glycol 400 | 150.0 mg |
| Acetic Acid | q.s. ad pH 5.0 |
| Water for injection solutions | ad 1.0 ml |

The active ingredient is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example D

Soft gelatin capsules containing the following ingredients can be manufactured in a conventional manner:

| Capsule contents | |
| --- | --- |
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titan dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
| --- | --- |
| Compound of formula (I) | 50.0 mg |
| Lactose, fine powder | 1015.0 mg |
| Microcristalline cellulose (AVICEL PH 102) | 1400.0 mg |
| Sodium carboxymethyl cellulose | 14.0 mg |
| Polyvinylpyrrolidon K 30 | 10.0 mg |
| Magnesiumstearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidon in water. The granulate is mixed with magnesiumstearate and the flavouring additives and filled into sachets.

Unless stated to the contrary, all compounds in the examples were prepared and characterized as described. All ranges recited herein encompass all combinations and subcombinations included within that range limit. All patents and publications cited herein are hereby incorporated by reference in their entirety.

The invention claimed is:

1. A compound of formula (I):

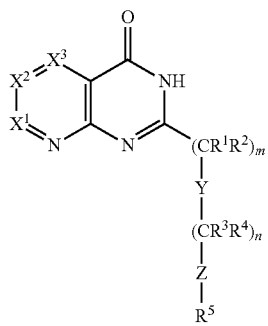

or a pharmaceutically acceptable salt thereof, wherein:
$X^1$ is N; $X^2$ is $C(R^7)$; and $X^3$ is $C(R^8)$; and wherein R7 and R8 independently from each other are selected from the group consisting of:
(1) hydrogen,
(2) halogen,
(3) lower-alkyl,
(4) fluoro-lower-alkyl,
(5) lower-alkoxy,
(6) fluoro-lower-alkoxy, and
(7) cycloalkyl;
Y is selected from the group consisting of:
(1) a single bond,
(2) O,
(3) $N(R^9)C(O)$,
(4) $C(O)NR^9$,
(5) $N(R^9)C(O)O$,
(6) $OC(O)NR^9$,
(7) $N(R^9)C(O)NR^{10}$,
(8) $N(R^9)SO_2$, and
(9) $SO_2N(R^9)$;
wherein $R^9$ and $R^{10}$ independently from each other are selected from the group consisting of hydrogen, lower-alkyl and fluoro-lower-alkyl;
Z is a single bond, or, if n is 1, 2, 3, 4, 5 or 6, Z can also be O;
$R^1$, $R^2$, $R^3$ and $R^4$ independently from each other are selected from the group consisting of:
(1) hydrogen,
(2) fluoro,
(3) lower-alkyl, and
(4) fluoro-lower-alkyl; or
$R^1$ and $R^2$ are bound together with the carbon atom to which they are attached to form a ring of 3 to 7 carbon atoms; or $R^3$ and $R^4$ are bound together with the carbon atom to which they are attached to form a ring of 3 to 7 carbon atoms;

$R^5$ is aryl or heteroaryl, which aryl or heteroaryl is optionally substituted with 1 to 3 substituents independently selected from the group consisting of:
(1) halogen,
(2) lower-alkyl,
(3) lower-alkoxy,
(4) fluoro-lower-alkyl,
(5) fluoro-lower-alkoxy,
(6) cycloalkyl,
(7) fluoro-cycloalkyl,
(8) cycloalkyl-oxy,
(9) C(O)OH,
(10) lower-alkoxy-C(O),
(11) $NH_2C(O)$,
(12) N(H,lower-alkyl)C(O),
(13) $N(lower-alkyl)_2C(O)$,
(14) OH,
(15) lower-alkyl-C(O)O,
(16) $NH_2$,
(17) N(H,lower-alkyl),
(18) $N(lower-alkyl)_2$,
(19) lower-alkyl-C(O)NH,
(20) lower-alkyl-C(O)N(lower-alkyl),
(21) $NH_2SO_2$,
(22) $N(H,lower-alkyl)SO_2$,
(23) $N(lower-alkyl)_2SO_2$,
(24) lower-alkyl-$SO_2$—NH,
(25) lower-alkyl-$SO_2$—N(lower-alkyl),
(26) cyano, and
(27) phenyl which is optionally substituted with 1 to 3 substituents independently selected from the group consisting of halogen, lower-alkyl, lower-alkoxy and fluoro-lower-alkyl;
m is 0, 1, 2 or 3; and n is 0, 1, 2, 3, 4, 5 or 6; wherein m+n is ≧1.

2. A compound according to claim 1, wherein Y is a single bond, O, $N(R^9)C(O)$, $N(R^9)C(O)O$, or $N(R^9)SO_2$.

3. A compound according to claim 1, wherein Y is O or $N(R^9)C(O)O$.

4. A compound according to claim 1, wherein Z is a single bond.

5. A compound according to claim 1, wherein $R^1$, $R^2$, $R^3$ and $R^4$ are hydrogen.

6. A compound according claim 1, wherein $R^5$ is phenyl or naphthyl, which phenyl or naphthyl is optionally substituted with 1 to 3 substituents independently selected from the group consisting of halogen, lower-alkyl and lower-alkoxy.

7. A compound according to claim 1, wherein $R^5$ is phenyl which is optionally substituted with 1 to 2 halogens.

8. A compound according to claim 1, wherein $R^5$ is phenyl, 3-chloro-phenyl, 2,5-difluoro-phenyl or 3-chloro-4-fluoro-phenyl.

9. A compound according to claim 1, wherein $R^7$ and $R^8$ independently of each other are hydrogen or halogen.

10. A compound according to claim 1, wherein $R^9$ and $R^{10}$ are hydrogen.

11. A compound according to claim 1, wherein m is 1, 2 or 3 and n is 0, 1, 2 or 3.

12. A compound according to claim 1, wherein m is 1 and n is 1 or 2.

13. A compound according to claim 1, selected from the group consisting of:
3-Chloro-7-[2-(3-chloro-phenyl)-ethoxymethyl]-6H-pyrimido[4,5-c]pyridazin-5-one,
7-[2-(3-Chloro-phenyl)-ethoxymethyl]-6H-pyrimido[4,5-c]pyridazin-5-one, 7-[2-(3-Chloro-4-fluoro-phenyl)-ethoxymethyl]-6H-pyrimido[4,5-c]pyridazin-5-one,
7-(2-Naphthalen-2-yl-ethoxymethyl)-6H-pyrimido[4,5-c]pyridazin-5-one,
7-(3-Phenyl-propyl)-6H-pyrimido[4,5-c]pyridazin-5-one,
7-(2-Benzyloxy-ethyl)-6H-pyrimido[4,5-c]pyridazin-5-one,
7-[2-(2-Fluoro-phenyl)-ethoxymethyl]-6H-pyrimido[4,5-c]pyridazin-5-one,
7-(3-Methoxy-phenoxymethyl)-6H-pyrimido[4,5-c]pyridazin-5-one,
N-(5-Oxo-5,6-dihydro-pyrimido[4,5-c]pyridazin-7-ylmethyl)-3-phenyl-propionamide,
(5-Oxo-5,6-dihydro-pyrimido[4,5-c]pyridazin-7-ylmethyl)-carbamic acid benzyl ester, and
4-Methyl-N-[2-(5-oxo-5,6-dihydro-pyrimido[4,5-c]pyridazin-7-yl)-ethyl]-benzenesulfonamide, or a pharmaceutically acceptable salt thereof.

14. A compound according to claim 1, selected from the group consisting of:
3-Chloro-7-[2-(3-chloro-phenyl)-ethoxymethyl]-6H-pyrimido[4,5-c]pyridazin-5-one,
7-[2-(3-Chloro-phenyl)-ethoxymethyl]-6H-pyrimido[4,5-c]pyridazin-5-one, and
7-[2-(3-Chloro-4-fluoro-phenyl)-ethoxymethyl]-6H-pyrimido[4,5-c]pyridazin-5-one,
or a pharmaceutically acceptable salt thereof.

15. A compound according to claim 1, selected from the group consisting of:
7-(3-Phenyl-propyl)-6H-pyrimido[4,5-c]pyridazin-5-one,
7-(2-Benzyloxy-ethyl)-6H-pyrimido[4,5-c]pyridazin-5-one,
7-[2-(2-Fluoro-phenyl)-ethoxymethyl]-6H-pyrimido[4,5-c]pyridazin-5-one, and
(5-Oxo-5,6-dihydro-pyrimido[4,5-c]pyridazin-7-ylmethyl)-carbamic acid benzyl ester, or a pharmaceutically acceptable salt thereof.

16. A compound according to claim 1, which is 7-[2-(3-Chloro-phenyl)-ethoxymethyl]-6H-pyrimido[4,5-c]pyridazin-5-one.

17. A pharmaceutical composition comprising a therapeutically effective amount of a compound of claim 1 and a pharmaceutically acceptable carrier.

* * * * *